US011547722B2

(12) United States Patent
Walter

(10) Patent No.: US 11,547,722 B2
(45) Date of Patent: Jan. 10, 2023

(54) BACTERICIDES AND ANTIFUNGAL AGENTS

(71) Applicant: Jean-Jacques Walter, Paris (FR)

(72) Inventor: Jean-Jacques Walter, Paris (FR)

( * ) Notice: Subject to any disclaimer, the term of this patent is extended or adjusted under 35 U.S.C. 154(b) by 508 days.

(21) Appl. No.: 16/612,885

(22) PCT Filed: May 14, 2018

(86) PCT No.: PCT/FR2018/000117
§ 371 (c)(1),
(2) Date: Nov. 12, 2019

(87) PCT Pub. No.: WO2018/206867
PCT Pub. Date: Nov. 15, 2018

(65) Prior Publication Data
US 2020/0163990 A1 May 28, 2020

(30) Foreign Application Priority Data
May 12, 2017 (FR) ..................................... 1754219

(51) Int. Cl.
| | | |
|---|---|---|
| *A61K 33/38* | (2006.01) | |
| *A61P 17/10* | (2006.01) | |
| *A61K 33/242* | (2019.01) | |
| *A61K 8/04* | (2006.01) | |
| *A61K 8/06* | (2006.01) | |
| *A61K 8/19* | (2006.01) | |
| *A61K 8/34* | (2006.01) | |
| *A61K 8/92* | (2006.01) | |
| *A61K 9/00* | (2006.01) | |
| *A61K 9/107* | (2006.01) | |
| *A61K 9/14* | (2006.01) | |
| *A61K 33/34* | (2006.01) | |
| *A61K 47/10* | (2017.01) | |
| *A61K 47/44* | (2017.01) | |
| *A61K 33/24* | (2019.01) | |

(52) U.S. Cl.
CPC .............. *A61K 33/38* (2013.01); *A61K 8/044* (2013.01); *A61K 8/062* (2013.01); *A61K 8/19* (2013.01); *A61K 8/345* (2013.01); *A61K 8/922* (2013.01); *A61K 9/0014* (2013.01); *A61K 9/107* (2013.01); *A61K 9/14* (2013.01); *A61K 33/24* (2013.01); *A61K 33/242* (2019.01); *A61K 33/34* (2013.01); *A61K 47/10* (2013.01); *A61K 47/44* (2013.01); *A61P 17/10* (2018.01)

(58) Field of Classification Search
None
See application file for complete search history.

(56) References Cited

U.S. PATENT DOCUMENTS

| | | |
|---|---|---|
| 2006/0246149 A1 | 11/2006 | Buchholz et al. |
| 2008/0233005 A1 | 9/2008 | Tichy et al. |
| 2010/0180413 A1 | 7/2010 | Jeong |
| 2013/0142886 A1 | 6/2013 | Singleton et al. |

FOREIGN PATENT DOCUMENTS

WO   2005077329 A1   8/2005

OTHER PUBLICATIONS

International Search Report, dated Oct. 23, 2018, from corresponding PCT application No. PCT/FR2018/000117.
Database GNPD [Online] Mintel; Miracellar Cleansing Water; XP002778168; Database Accession No. 4323129; Oct. 1, 2016.
Database GNPD [Online] Mintel; Gentle Exfoliating Cleansing Cream; XP002778169; Database Accession No. 337195; Sep. 1, 2015.
Database GNPD [Online] Mintel; Repairing Cream; XP002778170; Database Accession No. 3392947; Aug. 1, 2015.
Lee et al.; The Silver Nanoparticle (Nano-Ag): a New Model for Antifungal Agents; InTech XP055450559; Mar. 1, 2010.
Zawrah et al.; Antimicrobial Activities of Gold Nanoparticles against Major Foodborne Pathogens; Life Science Journal; vol. 8 XP055450763; Jan. 1, 2011.
Addae et al.; Investigation of antimicrobial activity of photothermal therapeutic gold/copper sulfide core/shell nanoparticles to bacterial spores and cells; Journal of Biological Engineering, Biodmed Central Ltd.; vol. 8, No. 1 XP021189648; Jun. 2, 2014.
International Preliminary Report on Patentability; dated Nov. 12, 2019; from corresponding PCT application No. PCT/FR2018/000117.

*Primary Examiner* — Nannette Holloman
(74) *Attorney, Agent, or Firm* — Nixon & Vanderhye

(57) ABSTRACT

Disclosed are a composition containing a transition metal, as well as a method of treatment of bacterial, or of fungal diseases using such composition. The composition functions as novel bactericides and antifungal agents. The transition metal may be in either soluble or insoluble form.

14 Claims, 6 Drawing Sheets

BACTERICIDES AND ANTIFUNGAL AGENTS

The present invention relates to the production of novel bactericides and fungicides.

There is a growing number of bacteria that have become resistant to known antibiotics, and the search for new antibiotics is stalling.

On the other hand, there are bacterial formations called biofilms, which are resistant to all known antibiotics.

Cosmetic products and certain medicines are formed by a pasty emulsion of water and oil. This emulsion is likely to be colonized by bacteria and molds. They are protected by adding parabens as a preservative at 0.4% to 0.8%. Parabens have disadvantages that lead to seek to replace them.

Moreover, in their use as an anti-acne agent, the current drugs (Epiduo, Aczone, Finacea, Acanya, and Ziana) have serious drawbacks: they cause dryness of the skin, itching, desquamation and slight edema, which often leads to the discontinuation of treatment. Moreover, they are teratogenic on the fetuses of pregnant women who use one of these current anti-acne agent.

One of the aims of the invention is therefore to provide new bactericides.

One of the aims of the invention is therefore to provide new antifungal agents

Another object of the invention is to use a transition metal in the treatment of acne.

The present invention relates to the use as a bactericidal or anti-fungal of a transition metal, or the use of a transition metal in the treatment of bacterial or fungal diseases, in particular acne.

By "use as bactericidal or use in the treatment of bacterial diseases" it is understood, within the meaning of the present invention, a use for the purpose of killing at least one bacterium. The bacteria concerned are gram-positive or gram-negative bacteria, in particular the bacteria concerned are chosen from *Staphylococcus aureus*, methicillin-resistant *Staphylococcus aureus* (MRSA), methicillin-sensitive *Staphylococcus aureus* (MSSA), *Propionibacterium acnes*, *Escherichia coli* pseudomonas. *Aeruginas*.

By "use as antifungal agents or use in the treatment of fungal diseases" it is understood, within the meaning of the present invention, a use for the purpose of killing at least one yeast, for example *Candida albicans*

Within the meaning of the present invention, it is understood that an "acne treatment" has a bactericidal action on a bacterium responsible for acne. In particular, the treatment of acne means a bactericidal action on *Propionibacterium acnes*, or an action on both *Propionibacterium acnes* and *Staphylococcus aureus*.

Within the meaning of the present invention, a bactericidal or antifungal agent means a substance whose Minimum Inhibitory Concentration is less than or equal to 0.2 g/l, between 0.1 and 0.2 g/l or less or equal to 0.1 g/l.

A first subject of the invention is a transition metal in insoluble form, in particular in the form of a transition metal with oxidation state 0 or in the form of a sulfide or a transition metal oxide, or in soluble form in particular salts of sulphates, nitrates or chlorides of the transition metal, for its use in the treatment of bacterial or fungal diseases, in particular acne.

Within the meaning of the invention, the term "transition metal" means a ring selected from the groups IVB, VB, VIB, VIIB, VIIIB, IB and IIB of the Mendeleev periodic table; preferentially a nucleus chosen from column IB.

Within the meaning of the present invention, it is understood by "use of a transition metal" the use of at least one transition metal. The present invention therefore also relates to the use of a mixture of transition metals, in particular a mixture of two or three transition metals.

Within the meaning of the invention, the term "insoluble" is intended to mean a powder which does not dissolve in water, that is to say the maximum concentration of which in aqueous solution is less than 0.5 mg.l$^{-1}$ at room temperature, that is to say at a temperature of about 25 C, and which is put into aqueous solution by the addition of an additive to form nanoparticles or complexes.

In the case of nanoparticles, the additive is a surfactant. Examples of surfactants include RX, X being a radical derived from an inorganic or organic acid, in particular $NO_3^-$, $SO_4^-$, $CH_3COO^-$, or halogen or any other acid radical; R is a C1-C20 alkyl trimethylammonium, in particular cetyltrimethylammonium or octyltrimethylammonium, in particular R1Xtrimethylammonium. The surfactant may also be a trimethyl (I) ammonium bromide in which R1 represents an alkyl of 6 to 20 carbon atoms and in particular 8, 9, 10, 1 1, 12, 13, 14, 15, 16, 17, or 18 carbon atoms, or also a polyethylene glycol, or a polyethylene glycol-dithiol.

Within the meaning of the present invention, the term "mineral acid" means an acid derived from a mineral or inorganic body, such as hydrochloric, sulfuric or nitric acid.

Within the meaning of the present invention, the term "organic acid" means an organic compound having acidic properties, such as the carboxylic acids of formula R2COOH, R2 being a hydrogen or an organic compound.

For the purpose of the present invention, the expression "C1-C20 alkyl" denotes a linear or branched, saturated acyclic carbon chain comprising 1 to 20 carbon atoms. Examples of C1 to C20 alkyls include methyl, ethyl, propyl, butyl, pentyl, hexyl or heptyl. The definition of propyl, butyl, pentyl, hexyl or heptyl includes all possible isomers. For example, the term butyl includes n-butyl, iso-butyl, sec-butyl and tert-butyl. The alkyl may be substituted at different positions by one or more functional groups such as halogen, alkoxyl, amino, nitro, cyano, trifluoromethyl or carboxylic ester.

In the case of complexes, the additive is a solubilizing agent selected from ammonia, citric acid, potassium dichromate or a mixture thereof. When the solubilizing agent is a mixture of ammonia and citric acid, ammonium citrate is formed; the solubilizing agent thus formed is then either ammonium citrate with citric acid if the citric acid is present in molar excess relative to the ammonia, or ammonium citrate with ammonia if ammonia is introduced in molar excess relative to citric acid.

In the insoluble form of the paraben substitute of the invention are therefore grouped the nanoparticles and the transition metal complexes as defined above.

A "soluble" salt, in the sense of the invention, is, on the contrary, a powder which solubilizes in contact with water, without the addition of an additive, that is to say with a maximum concentration of aqueous solution is greater than 0.5 mg.l$^{-1}$. In the soluble form of the paraben substitute of the invention are the salts and oxides of transition metals as defined above.

According to one particular embodiment, the invention relates to a transition metal as described above, in insoluble form, in particular in the form of a sulfide or of an oxide of the transition metal, in particular chosen from column IB of Mendeleev's Table, in particular selected from copper, silver and gold, for use in the treatment of bacterial or fungal diseases, in particular acne.

According to one particular embodiment, the invention relates to a transition metal as described above, in soluble form in particular salts of sulphates, nitrates or chlorides of the transition metal, in particular chosen from column IB of Mendeleev's Table, in particular selected from copper, silver and gold, for use in the treatment of bacterial or fungal diseases, in particular acne.

According to an advantageous embodiment, the invention relates to a transition metal as described above, in insoluble form, said transition metal in insoluble form being put into aqueous solution by the formation of nanoparticles or by the formation of a complex, for its use in the treatment of bacterial or fungal diseases, in particular acne.

Within the meaning of the present invention, the term "put into aqueous solution" corresponds to the formation of an aqueous solution, an emulsion or an aqueous suspension whose transition metal concentration as described above is greater than 0.5 mg.l$^{-1}$ Within the meaning of the present invention, "complex" is understood to mean a metal cation, formed from a transition metal as defined above, bound to several atoms, ions or molecules called ligands. Examples of ligands include water and the additives defined above.

According to an advantageous embodiment, the invention relates to a transition metal as described above, in insoluble form, said transition metal in insoluble form being put into aqueous solution by the formation of nanoparticles, for its use in the treatment of bacterial or fungal diseases, in particular acne.

According to an advantageous embodiment, the invention relates to a transition metal as described above, in insoluble form, said transition metal in insoluble form being put into aqueous solution by the formation of nanoparticles, for its use in the treatment of bacterial diseases, in particular acne.

According to an advantageous embodiment, the invention relates to a transition metal as described above, in insoluble form, said transition metal in insoluble form being put into aqueous solution by the formation of nanoparticles, for its use in the treatment of acne.

According to a particular embodiment, the invention relates to a transition metal as described above, contained in a structure consisting of a core containing said transition metal, surrounded by a surfactant shell, said surfactant being chosen in particular from RX, X being a radical derived from a mineral or organic acid, in particular $NO_3^-$, $SO_4^-$, $CH_3COO^-$, or halogen or any other acid radical; R being a C1-C20 alkyl trimethylammonium, in particular cetyltrimethylammonium or octyltrimethylammonium, a polyethylene glycol, or a polyethylene glycol-dithiol, for its use in the treatment of bacterial or fungal diseases, in particular acne.

Within the meaning of the present invention, the term "surfactant" is intended to mean a molecule which has a hydrophilic end and another hydrophobic end.

As defined above, the surfactant may be a trimethylammonium bromide R1 in which R1 represents an alkyl of 6 to 20 carbon atoms and in particular 8, 9, 10, 1 1, 12, 13, 14, 15, 16, 17, or 18 carbon atoms. Examples of surfactants include CTAB (cetyltrimethylammonium bromide; Br[N(CH$_3$)$_3$(C$_{16}$H$_{33}$)], OTAB (octyltrimethylammonium bromide; Br[N(CH$_3$)$_3$(C$_8$H$_{17}$)]), RX, X being a radical derived from a mineral or organic acid, in particular $NO_3^-$, $SO_4^-$, $CH_3COO^-$, or a halogen or any other acid radical; R being a C1-C20 alkyl trimethylammonium, in particular cetyltrimethylammonium or octyltrimethylammonium, in particular R1Xtrimethylammonium, or PEG-dithiol (polyethylene glycol comprising terminal thiol groups) and PEG-600 (polyethylene glycol with an average molecular weight is 600 g/mol). Preferably, the surfactant used to stabilize the nanoparticles is CTAB, or CTAX, X being an acid, preferably strong, in particular nitric or sulfuric acid.

The nanoparticles having a structure consisting of a core containing the transition metal, surrounded by a surfactant shell, measure about 2 to 4 nanometers in diameter. The core diameter is about 60% of the total diameter, and the thickness of the shell is about 40% of the total diameter. The mass of the core represents about 57% of the total mass of the nanoparticle and the shell about 43% of the total mass.

According to a particular embodiment, the invention relates to a transition metal as described above, chosen from column IB of Mendeleev's Table, in particular chosen from copper, silver and gold, for its use in the treatment of bacterial or fungal diseases, in particular acne.

Within the meaning of the present invention, the transition metal of Mendeleev's Table column IB is at the oxidation state of 0, +I, +II or +III. In particular, the invention relates to the use of a transition metal selected from Cu (O), Cu (II), Ag (O), Ag (I), Au (O) or Au (III).

According to one particular embodiment, the invention relates to a transition metal as described above, chosen from copper, silver and gold, and being in the form of a sulfide, in particular in the form of a complex or in the form of nanoparticles, for use in the treatment of bacterial or fungal diseases, in particular acne. According to a particular embodiment, the invention relates to a transition metal as described above, selected from copper, silver and gold, being at oxidation state 0 and in the form of nanoparticles, for its use in the treatment of bacterial or fungal diseases, in particular acne.

According to one particular embodiment, the invention relates to a transition metal as described above, chosen from copper, silver and gold, being in the form of a soluble salt, for its use in the treatment of bacterial or fungal diseases, in particular acne.

According to an advantageous embodiment, the invention relates to a transition metal as described above, in a composition containing water, in particular comprising in the order of 1 to 200 mg, in particular 1 to 5, 5 to 10, 10 to 50, 50 to 75, 75 to 100, 100 to 125, 125 to 150, 150 to 175, 175 to 200 mg of transition metal per liter of composition, for use in the treatment of bacterial diseases or fungal, in particular acne.

According to one particular embodiment, the invention relates to a transition metal in a composition as defined above, said composition containing water being an aqueous solution, for its use in the treatment of bacterial or fungal diseases, in particular acne.

According to one particular embodiment, the invention relates to a transition metal in a composition as defined above, said composition containing water being an emulsion or a suspension, for its use in the treatment of bacterial or fungal diseases, in particular acne.

According to one particular embodiment, the invention relates to a transition metal in a composition as defined above, said composition containing water being an oil-in-water or water-in-oil emulsion, in particular comprising copper, silver or gold in the form of nanoparticles, for use in the treatment of bacterial or fungal diseases, in particular acne.

A second subject of the invention is a transition metal in insoluble form, in particular in the form of a transition metal with oxidation state 0 or in the form of a sulfide or of a transition metal oxide, or in soluble form in particular salts of sulphates, nitrates or chlorides of the transition metal, for its use in the treatment of bacterial diseases, in particular acne.

According to one particular embodiment, the invention relates to a transition metal as described above, in insoluble form, in particular in the form of a sulfide or of an oxide of the transition metal, in particular chosen from column IB of Mendeleev's Table, in particular selected from copper, silver and gold for its use in the treatment of bacterial diseases, in particular acne.

According to one particular embodiment, the invention relates to a transition metal as described above, in soluble form in particular salts of sulphates, nitrates or chlorides of the transition metal, in particular chosen from column IB of Mendeleev's Table, in particular selected from copper, silver and gold, for its use in the treatment of bacterial diseases, in particular acne.

According to an advantageous embodiment, the invention relates to a transition metal as described above, in insoluble form, said transition metal in insoluble form being put into aqueous solution by the formation of nanoparticles or by the formation of a complex, for its use in the treatment of bacterial diseases, in particular acne.

According to a particular embodiment, the invention relates to a transition metal as described above, contained in a structure consisting of a core containing said transition metal, surrounded by a surfactant shell, said surfactant being chosen in particular from RX, X being a radical derived from an inorganic or organic acid, in particular $NO_3^-$, $SO_4^-$, $CH_3COO^-$, or halogen or any other acidic radical, R being a C1-C20 alkyl trimethylammonium, cetyltrimethylammonium or octyltrimethylammonium, polyethylene glycol, or polyethylene glycol-dithiol, for its use in the treatment of bacterial diseases, in particular acne.

According to a particular embodiment, the invention relates to a transition metal as described above, chosen from column IB of Mendeleev's Table, in particular chosen from copper, silver and gold, for its use in the treatment of bacterial diseases, in particular acne.

According to one particular embodiment, the invention relates to a transition metal as described above, chosen from copper, silver and gold, and being in the form of a sulfide, in particular in the form of a complex or in the form of nanoparticles, for its use in the treatment of bacterial diseases, in particular acne.

According to a particular embodiment, the invention relates to a transition metal as described above, selected from copper, silver and gold, being at oxidation state 0 and in the form of nanoparticles, for its use in the treatment of bacterial diseases, in particular acne. According to one particular embodiment, the invention relates to a transition metal as described above, chosen from copper, silver and gold, being in the form of a soluble salt, for its use in the treatment of bacterial diseases, in particular acne.

According to an advantageous embodiment, the invention relates to a transition metal as described above, in a composition containing water, in particular comprising in the order of 1 to 200 mg, in particular 1 to 5, 5 to 10, 10 to 50, 50 to 75, 75 to 100, 100 to 125, 125 to 150, 150 to 175, 175 to 200 mg of transition metal per liter of composition, for use in the treatment of bacterial diseases, in particular acne.

According to one particular embodiment, the invention relates to a transition metal in a composition as defined above, said composition containing water being an aqueous solution, for its use in the treatment of bacterial diseases, in particular the acne.

According to one particular embodiment, the invention relates to a transition metal in a composition as defined above, said composition containing water being an emulsion or a suspension, for its use in the treatment of bacterial diseases, in particular acne.

According to one particular embodiment, the invention relates to a transition metal in a composition as defined above, said composition containing water being an oil-in-water or water-in-oil emulsion, paraben-free and in particular comprising copper, silver or gold in the form of nanoparticles, for use in the treatment of bacterial diseases, in particular acne.

Another subject of the invention is a transition metal in insoluble form, in particular in the form of a transition metal with oxidation state 0 or in the form of a sulfide or a transition metal oxide, or in soluble form in particular salts of sulphates, nitrates or chlorides of the transition metal, for its use as an antibacterial or antifungal agent, in particular as an anti-acne agent.

According to a particular embodiment, the invention relates to a transition metal as described above, in insoluble form, said transition metal in insoluble form being put into aqueous solution by the formation of nanoparticles or by the formation of a complex, for its use as an antibacterial or antifungal agent, in particular as an anti-acne agent.

According to a particular embodiment, the invention relates to a transition metal as described above, contained in a structure consisting of a core containing said transition metal, surrounded by a surfactant shell, said surfactant being chosen in particular from RX, X being a radical derived from a mineral or organic acid, in particular $NO_3^-$, $SO_4^-$, $CH_3COO^-$, or halogen or any other acid radical; R being a C1-C20 alkyl trimethylammonium, in particular cetyltrimethylammonium or octyltrimethylammonium, a polyethylene glycol, or a polyethylene glycol-dithiol, for its use as an antibacterial or antifungal agent, in particular as an anti-acne agent.

According to one particular embodiment, the invention relates to a transition metal as described above, chosen from Mendeleev's column IB, in particular chosen from copper, silver and gold, for its use as an antibacterial or antifungal agent, in particular as an anti-acne agent.

According to one particular embodiment, the invention relates to a transition metal as described above, chosen from copper, silver and gold, and being in the form of a sulfide, in particular in the form of a complex or in the form of nanoparticles, for its use as an antibacterial or antifungal agent, in particular as an anti-acne agent.

According to a particular embodiment, the invention relates to a transition metal as described above, selected from copper, silver and gold, being at oxidation state 0 and in the form of nanoparticles, for its use as an antibacterial or antifungal agent, in particular as an anti-acne agent.

According to one particular embodiment, the invention relates to a transition metal as described above, chosen from copper, silver and gold, being in the form of a soluble salt, for its use as an antibacterial or antifungal agent, in particular as an anti-acne agent.

According to a particular embodiment, the invention relates to a transition metal as described above, in a composition containing water, in particular comprising from 1 to 200 mg, in particular 1 to 5, to 10, 10 to 50, 50 to 75, 75 to 100, 100 to 125, 125 to 150, 150 to 175, 175 to 200 mg of transition metal per liter of composition, for its use as an antibacterial or antifungal agent, in particular as an anti-acne agent.

According to a particular embodiment, the invention relates to a transition metal in a composition as defined above, said composition containing water being an aqueous solution, for its use as an antibacterial or antifungal agent, in particular as an anti-acne agent.

According to one particular embodiment, the invention relates to a transition metal in a composition as defined above, said composition containing water being an emulsion or a suspension, for its use as an antibacterial or antifungal agent, in particular as an anti-acne agent. According to one particular embodiment, the invention relates to a transition metal in a composition as defined above, said composition containing water being an oil-in-water or water-in-oil emulsion and in particular comprising copper, silver or gold in the form of nanoparticles, for its use as an antibacterial or antifungal agent, in particular as an anti-acne agent.

Another subject of the invention is a pharmaceutical or veterinary composition containing a transition metal as described above.

According to a particular embodiment, the invention relates to a pharmaceutical or veterinary composition as described above, wherein the transition metal is at a dose of 1 mg to 1 g, in particular 1 to 10 mg, 10 to 50 mg, 50 to 100 mg, 100 to 500 mg, 500 mg to 1 g, of transition metal per liter of composition.

According to a particular embodiment, the invention relates to a pharmaceutical or veterinary composition as described above, comprising as excipients at least one vegetable oil, in particular argan oil, grape seed, avocado, hemp or apricot kernels.

According to a particular embodiment, the invention relates to a pharmaceutical or veterinary composition as described above, whose form of administration is topical.

Within the meaning of the invention, the term "topical administration" means an administration on an external point of the body, or on a surface of the body such as the skin or the mucous membranes, having a direct action at the point of administration.

Another object of the invention is the use of a transition metal as described above for cosmetic use.

Another object of the invention is a cosmetic composition containing a transition metal as described above.

According to one particular embodiment, the invention relates to a cosmetic composition as described above, comprising in the order of 1 to 200 mg, in particular 1 to 5, 5 to 10, 10 to 50, 50 to 75, 75 to 100, 100 to 125, 125 to 150, 150 to 175, 175 to 200 mg of transition metal per liter of composition.

Another subject of the invention is a method for treating bacterial or fungal diseases, in particular acne, comprising the topical administration of a transition metal in insoluble form, in particular in the form of a transition metal in the form of a transition metal. state of oxidation 0 or in the form of a sulfide or an oxide of the transition metal, or in soluble form, in particular salts of sulphates, nitrates or chlorides of the transition metal.

According to a particular embodiment, the invention relates to a method of treating bacterial or fungal diseases, in particular acne, comprising the topical administration of a transition metal as described above in insoluble form, said transition metal in insoluble form being put into aqueous solution by the formation of nanoparticles or by the formation of a complex.

According to a particular embodiment, the invention relates to a method of treating bacterial or fungal diseases, in particular acne, comprising the topical administration of a transition metal as described above contained in a structure constituted by a core containing said transition metal, surrounded by a surfactant shell, said surfactant being in particular selected from RX, X being a radical derived from an inorganic or organic acid, in particular $NO_3^-$, $SO_4^-$, $CH_3COO^-$, or a halogen or other acid radical; R being a C1-C20 alkyl trimethylammonium, in particular cetyltrimethylammonium or octyltrimethylammonium, a polyethylene glycol, or a polyethylene glycol-dithiol.

According to a particular embodiment, the invention relates to a method for treating bacterial or fungal diseases, in particular acne, comprising the topical administration of a transition metal as described above, chosen from the column IB of Mendeleev's Table, in particular selected from copper, silver and gold.

According to a particular embodiment, the invention relates to a method for treating bacterial or fungal diseases, comprising the topical administration to humans or animals, in particular the horse, of a transition metal in the form of insoluble, in particular in the form of a transition metal with oxidation state 0 or in the form of a sulfide or an oxide of the transition metal, or in soluble form, in particular salts of sulphates, nitrates or chlorides of the transition metal.

According to a particular embodiment, the invention relates to a method for treating bacterial or fungal diseases, comprising the topical administration to humans or animals, in particular the horse, of a transition metal such as described above in insoluble form, said transition metal in insoluble form being put into aqueous solution by the formation of nanoparticles or by the formation of a complex.

According to a particular embodiment, the invention relates to a method for treating bacterial or fungal diseases, comprising the topical administration to humans or animals, in particular the horse, of a transition metal such as described above contained in a structure consisting of a core containing said transition metal, surrounded by a surfactant shell, said surfactant being in particular chosen from an RX, X being a radical derived from a mineral or organic acid, in in particular $NO_3^-$, $SO_4^-$, $CH_3COO^-$, or halogen or any other acid radical; R being a C1-C20 alkyl trimethylammonium, in particular cetyltrimethylammonium or octyltrimethylammonium, a polyethylene glycol, or a polyethylene glycol-dithiol.

According to a particular embodiment, the invention relates to a method for treating bacterial or fungal diseases, comprising the topical administration to humans or animals, in particular the horse, of a transition metal such as described above, chosen from column IB of Mendeleev's Table, in particular chosen from copper, silver and gold.

Another object of the invention is to replace the paraben present as a preservative in food, cosmetic and/or pharmaceutical compositions.

Another object of the invention is to use a transition metal to replace the paraben present as a preservative in food, cosmetic and/or pharmaceutical compositions.

Another object of the invention is to provide a composition free of paraben and comprising transition metal sulfides used as a preservative.

In another subject, the present invention relates to the use as paraben substitute of a transition metal.

It is understood within the meaning of the invention, by "paraben", an alkyl parahydroxybenzoate, that is to say an ester, having broad-spectrum bactericidal and fungicidal properties. The antibacterial and antifungal properties of parabens make them generally used as a preservative in cosmetics, medicines and foods.

By "use as a paraben substitute" it is understood, within the meaning of the present invention, a use to replace the parabens used as a preservative because of their antibacterial and/or antifungal properties.

According to an advantageous embodiment, the invention relates to the use as a substitute of paraben of a transition metal in insoluble form, in particular in the form of a transition metal with oxidation state 0 or in the form of sulfide or of an oxide of the transition metal, or in soluble form in particular salts of sulphates, nitrates or chlorides of the transition metal. In the case of nanoparticles, the additive is a surfactant. Examples of surfactants include RX, X being a radical derived from an inorganic or organic acid, in particular $NO_3^-$, $SO_4^-$, $CH_3COO^-$, or halogen or any other acid radical; R is a C1-C20 alkyl trimethylammonium, in particular cetyltrimethylammonium or octyltrimethylammonium, in particular R1Xtrimethylammonium. The surfactant may also be a trimethylR ammonium bromide in which R1 represents an alkyl of 6 to 20 carbon atoms and in particular 8, 9, 10, 1 1, 12, 13, 14, 15, 16, 17, or 18 carbon atoms.

Examples of surfactants include CTAB (cetyltrimethylammonium bromide; $Br[N(CH_3)_3(C_{16}H_{33})]$, OTAB (octyltrimethylammonium bromide; $Br[N(CH_3)_3(C_8H_{17})]$), PEG-dithiol (Polyethylene glycol comprising terminal thiol functions) and PEG-600 (polyethylene glycol whose average molar mass is 600 g/mol).

According to an advantageous embodiment, the invention relates to the use as a substitute of paraben of a transition metal in insoluble form, in particular in the form of a transition metal with oxidation state 0, provided that when the metal is silver, it is not deposited on the surface of a polymer, or in the form of a sulfide or an oxide of the transition metal, or in soluble form in particular salts of sulphates, nitrates or chlorides of the transition metal.

According to another advantageous embodiment, the invention relates to the use, as a paraben substitute, of a transition metal in insoluble form, in particular in the form of a transition metal with oxidation state of 0, in particular chosen from Mendeleev's IB column, in particular chosen from copper, silver and gold, provided that when the metal is silver, it is not deposited on the surface of a polymer, According to another advantageous embodiment, the invention relates to the use as a substitute of paraben, of a transition metal in insoluble form, in particular in the form of a sulfide or an oxide of the transition metal, in particular chosen from the column IB of Mendeleev's Table, in particular selected from copper, silver and gold.

According to another advantageous embodiment, the invention relates to the use, as a substitute of paraben, of a transition metal in soluble form, in particular salts of sulphates, nitrates or chlorides of the transition metal, in particular chosen from column IB of Mendeleev's Table, in particular chosen from copper, silver and gold.

According to one embodiment, the diameter of the nanoparticles of the invention is from 1 to 10 nm, in particular from 1 to 5 nm, in particular from 2 nm to 4 nm.

According to another advantageous embodiment, the invention relates to the use as a substitute of paraben, of a transition metal in insoluble form, said transition metal in insoluble form being put into aqueous solution by the formation of nanoparticles or by the formation of a complex.

According to another advantageous embodiment, the invention relates to the use as a substitute of paraben, of a transition metal, said transition metal being contained in a structure consisting of a core containing said transition metal, surrounded by a surfactant shell, said surfactant being in particular chosen from an RX, X being a radical derived from a mineral or organic acid, in particular $NO_3^-$, $SO_4^-$, $CH_3COO^-$, or a halogen or any other acidic radical; R being a C1-C20 alkyl trimethylammonium, in particular cetyltrimethylammonium or octyltrimethylammonium, a polyethylene glycol, or a polyethylene glycol-dithiol.

According to another advantageous embodiment, the invention relates to the use as a substitute of paraben of a transition metal selected from column IB of Mendeleev's Table, in particular chosen from copper, silver and gold.

According to another advantageous embodiment, the invention relates to the use as a substitute of paraben of a transition metal selected from copper, silver and gold, and being in the form of a sulfide.

According to another advantageous embodiment, the invention relates to the use as a paraben substitute of a transition metal chosen from copper, silver and gold, being in the form of a sulfide and in the form of a complex..

Sulfides of gold, silver and copper, insoluble without additives, are soluble in the form of complexes.

For copper sulfide SCu, whose maximum concentration in aqueous solution is 0.33 mg/l, the addition of ammonia as an additive makes it possible to reach an aqueous concentration of Cu at least equal to 0.2 g/l.

For silver sulfide $SAg_2$, the maximum concentration of aqueous solution of which is soluble at $6,2.10^{-15}$ mg/l, the addition of citric acid or a mixture of citric acid and ammonia as an additive makes it possible to reach an aqueous concentration of Ag at least equal to 0.2 g/l.

For $S_3Au_2$ gold sulfide, the aqueous concentration without additive is undetectable. The addition of either potassium dichromate alone or an equimolar mixture of potassium dichromate and ammonia makes it possible to reach an aqueous Au concentration of at least 0.2 g/l. According to another advantageous embodiment, the invention relates to the use as a paraben substitute of a transition metal selected from copper, silver and gold, being in the form of sulfide and in the form of nanoparticles.

Within the meaning of the present invention, when the transition metal is in the form of copper sulfide nanoparticles, silver sulfide nanoparticles or gold sulfide nanoparticles, the transition metal presents, respectively, an oxidation state of +II, +I and +III, i.e., Cu (II), Ag (I) and Au (III).

According to another advantageous embodiment, the invention relates to the use, as paraben substitute, of a transition metal chosen from copper, silver and gold, being at oxidation state 0 and in the form of nanoparticles.

According to another advantageous embodiment, the invention relates to the use as a substitute of paraben of a transition metal selected from copper, silver and gold, being in the form of soluble salt.

According to another advantageous embodiment, the invention relates to the use of a transition metal in a composition containing water.

According to another advantageous embodiment, the invention relates to the use of a transition metal in a composition containing water and a reducing agent.

Within the meaning of the present invention, the term "reducing agent" is intended to mean a compound capable of reducing the transition metal salt used during the formation of the transition metal nanoparticles as described above and of preventing the oxidation of the transition metal during its use as described above. An example of a reducing agent in the meaning of the invention is glycerol in a basic medium (pH=14), preferably glycerol in the presence of NaOH. The reduction is carried out at pH 14, and once the metal nanoparticles have been formed, the solution is neutralized and brought back to pH 7. According to another advantageous embodiment, the invention relates to the use of a transition metal in a composition containing water, said composition comprising in the order of $10^{-6}$ gram of paraben substitute per gram of decomposition.

Within the meaning of the present invention, it is understood by "of the order of $10^{-6}$ gram" an approximate range of values, which may also be formulated by a range ranging from $10^{-6}$ to $10^{-7}$ g.

This range of concentrations represents 100 to 10,000 times less product than when using parabens. (Parabens are used at concentrations of 4 to 8 per 1000 outside Europe, and 3 times less in Europe).

According to another advantageous embodiment, the invention relates to the use of a transition metal in a composition. containing water, wherein the water-containing composition is an emulsion or a suspension.

According to another advantageous embodiment, the invention relates to the use of a transition metal in a composition containing water, wherein the composition containing water is an oil-in-water emulsion or water-in-oil.

According to one embodiment, the percentage of water relative to the amount of oil present in these emulsions is from 65 to 99%, preferably from 70 to 95%, in particular from 70 to 80% of water.

According to another advantageous embodiment, the invention relates to the use as a paraben substitute of a transition metal in a food or cosmetic or pharmaceutical product.

The invention also relates to a composition in the form of an oil-in-water or water-in-oil emulsion, free of parabens, comprising copper sulfide, silver sulfide or gold sulfide; in particular, said composition comprising copper sulfide.

According to an advantageous embodiment, the invention relates to a composition in which the copper sulfide, silver sulfide or gold sulfide forms a complex or nanoparticles.

According to an advantageous embodiment, the composition of the invention comprises copper sulfide, silver sulfide or gold sulfide, in the form of complexes or nanoparticles as defined above, said composition also comprising water and an additive.

According to an advantageous embodiment, the composition of the invention comprises copper sulfide, silver sulfide or gold sulfide, in the form of a complex as defined above, said composition also comprising water and an additive, said additive being selected from ammonia, citric acid, potassium dichromate or a mixture thereof.

According to an advantageous embodiment, the composition of the invention comprises copper sulfide, silver sulfide or gold sulfide, in the form of nanoparticles as defined above, said composition also comprising water and an additive, said additive being CTAB.

The invention also relates to a composition in the form of an oil-in-water or water-in-oil emulsion, free of parabens, comprising copper, silver or gold in the form of nanoparticles. According to one particular embodiment, the composition of the invention in the form of an oil-in-water or water-in-oil emulsion, free of parabens, comprising copper, silver or gold in the form of nanoparticles, also comprises an additive such as CTAB and a reducing agent such as glycerol in basic medium, in particular glycerol in the presence of NaOH at pH 14. The reduction is carried out at pH 14, and once the metal nanoparticles have been formed, the solution is neutralized and brought back to pH 7.

The present invention also relates to a transition metal for use as a bactericide, or as an antifungal agent.

In a second subject, the present invention relates to a transition metal for use in the treatment of acne.

The present invention also relates to a process for the preparation of transition metal nanoparticles and transition metal sulfide nanoparticles. The process for preparing the soluble transition metal sulfide complexes of the invention is described in Examples 1 to 3.

Thus, in a third subject, the present invention relates to a method (I) for preparing a bactericide comprising a transition metal in the form of nanoparticles of said transition metal, said process comprising a step of reducing the transition metal, in presence of an additive in an aqueous solution at pH 14 comprising glycerol. The reduction is carried out at pH 14, and once the nanoparticles of metals have been formed, the solution is neutralized and brought back to pH 7.

In particular, in the process (I) of the invention, the transition metal is selected from column IB of Mendeleev's Table, in particular chosen from copper (0), silver (0) and gold (0).

In particular, in process (I) of the invention, the transition metal is in the form of a metal salt before the reduction step. The metal salt is in particular chosen from copper (II), in particular copper nitrate $Cu(NO_3)_2$, silver (I), in particular silver nitrate $Ag(NO_3)$, and gold (Ill), in particular gold chloride $AuCl_3$.

In particular, in process (I) of the invention, the aqueous solution at pH 14 comprises water, glycerol and a base, in particular a hydroxide, in particular NaOH. The reduction is carried out at pH 14, and once the nanoparticles of metals have been formed, the solution is neutralized and brought back to pH 7.

In this process (I), the additive is a surfactant. Examples of surfactants include RX, X being a radical derived from an inorganic or organic acid, in particular $NO_3^-$, $SO_4^-$, $CH_3COO^-$, or halogen or any other acid radical; R is a C1-020 alkyl trimethylammonium, in particular cetyltrimethylammonium or octyltrimethylammonium, in particular R1Xtrimethylammonium. The surfactant may also be a trimethylri ammonium bromide in which R1 represents an alkyl of 6 to 20 carbon atoms and in particular 8, 9, 10, 1 1, 12, 13, 14, 15, 16, 17, or 18 carbon atoms. Examples of surfactants include CTAB (cetyltrimethylammonium bromide; $Br[N(CH_3)_3(C_{16}H_{33})]$, PEG-dithiol (polyethylene glycol in particular terminal thiol functions) and PEG-600 (polyethylene glycol with molar mass average is 600 g/mol).

The concentration of glycerol is from 0.8 to 2.2 M, in particular from 1 to 2 M, in particular from 1 to 1, 85 M in water after the step of reduction of the transition metal.

The process as described above is carried out either at 0° C., at room temperature, or at a temperature of 60 to 100° C., in particular from 80 to 100° C.

According to one particular embodiment, the process (I) of the invention comprises:
- a step of forming a solution A comprising the transition metal in the form of a metal salt, an additive and water;
- a step of forming an aqueous solution B at pH 14 comprising glycerol;
- a step of reducing the transition metal by adding solution A to aqueous solution B to form a suspension of nanoparticles;
- a neutralization step of the nanoparticle suspension obtained in the preceding step by the addition of an acid.

In particular, in the neutralization step of the process (I) of the invention, the acid is an inorganic acid, in particular HCl. Within the meaning of the invention, the term "neutralization" is intended to mean the passage of a basic solution, whose pH is from 8 to 14, to a solution at pH 7.

The concentration of metal salt during the formation of solution A is from 0.001 to 0.5 M, in particular from 0.01 to 0.04 M, in particular 0.013 M, 0.023 M or 0.04 M.

The concentration of additive during the formation of solution A is from 0.01 to 0.05 M, in particular from 0.02 to 0.04 M, in particular 0.02 M or 0.037 M.

According to one particular embodiment, the process (I) of the invention comprises:
- a step of forming a solution A comprising the transition metal in the form of a copper (II) salt, CTAB and water;
- a step of forming an aqueous solution B at pH 14 comprising glycerol;
- a step of reducing the transition metal by adding the solution A to the aqueous solution B to form a suspension of copper nanoparticles (0);
- a step of neutralizing the suspension of copper nanoparticles (0) obtained in the preceding step by the addition of HCl.

According to one particular embodiment, the process (I) of the invention comprises:
- a step of forming a solution A comprising the transition metal in the form of a silver salt (I), CTAB and water;
- a step of forming an aqueous solution B at pH 14 comprising glycerol;
- a step of reducing the transition metal by the addition of the solution A to the aqueous solution B to form a suspension of silver nanoparticles (0);
- a neutralization step of the suspension of silver nanoparticles (0) obtained in the previous step by the addition of HCl.

According to one particular embodiment, the process (I) of the invention comprises:
- a step of forming a solution A comprising the transition metal in the form of a gold salt (III), CTAB and water;
- a step of forming an aqueous solution B at pH 14 comprising glycerol;
- a step of reducing the transition metal by the addition of solution A to aqueous solution B to form a suspension of gold nanoparticles (0);
- a neutralization step of the suspension of gold nanoparticles (0) obtained in the previous step by the addition of HCl.

The optimal conditions for the preparation of transition metal nanoparticles according to the invention can be determined by those skilled in the art, in particular in view of Examples 8 to 10 of the present invention.

According to an advantageous embodiment, the invention relates to nanoparticles obtained by the process (I).

According to a fourth subject, the present invention relates to a method (II) for preparing a bactericide comprising a transition metal, said transition metal being in the form of a sulfide nanoparticle of said transition metal, said method comprising a step precipitation of a soluble salt of the transition metal in the presence of sodium sulfide $Na_2S$.

In particular, in the process (II) of the invention, the soluble salt of the transition metal is selected from copper (II), in particular copper sulphate $Cu(SO_4)$ or copper nitrate $Cu(NO_3)_2$, silver (I), in particular silver nitrate $Ag(NO_3)$, and gold (III), in particular gold chloride $AuCl_3$.

In this process (II), the additive is a surfactant. Examples of surfactants include RX, X being a radical derived from a mineral or organic acid, in particular $NO_3^-$, $SO_4^-$, $CH_3COO^-$, or halogen or any other acid radical; R is a C1-C20 alkyl trimethylammonium, in particular cetyltrimethylammonium or octyltrimethylammonium, in particular R1Xtrimethylammonium. The surfactant may also be a R1trimethyl ammonium bromide in which R1 represents an alkyl of 6 to 20 carbon atoms and in particular 8, 9, 10, 1 1, 12, 13, 14, 15, 16, 17, or 18 carbon atoms. Examples of surfactants include CTAB (cetyltrimethylammonium bromide; $Br[N(CH_3)_3(C_{16}H_{33})]$, OTAB (octyltrimethylammonium bromide; $Br[N(CH_3)_3(C_8H_{17})]$), PEG-dithiol (polyethylene glycol comprising terminal thiol functions) and PEG-600 (polyethylene glycol whose average molar mass is 600 g/mol).

According to a particular embodiment, the method (II) of the invention comprises:
- a step of forming a solution A comprising the transition metal in the form of a soluble salt of the transition metal, an additive and water;
- a step of forming a solution B comprising $Na_2S$ and water;
- a step of precipitating the soluble salt of the transition metal by adding solution A to solution B to form a suspension of metal sulfide nanoparticles;

In particular, in the neutralization step of the process (II) of the invention, the acid is an inorganic acid, in particular HCl. Within the meaning of the invention, the term "neutralization" is intended to mean the passage of a basic solution, whose pH is from 8 to 14, to a solution at pH 7.

The concentration of metal salt during the formation of solution A is from 0.001 to 0.5 M, in particular from 0.01 to 0.03 M, in particular 0.013 M, 0.023 M or 0.025 M.

The concentration of additive during the formation of solution A is from 0.01 to 0.05 M, in particular from 0.02 to 0.04 M, in particular 0.037 M. The molar concentration of the additive is 0, 5 times that of metallic salt The concentration of $Na_2S$ is from 0.001 to 0.02 M, in particular from 0.003 to 0.02 M, in particular 0.003 M, 0.0065 M or 0.0185 M in water after the formation step of solution B. The concentration of $Na_2S$ is the stoichiometric concentration for the formation of the insoluble salt. If the salt is $SO_4Cu$, $Na_2S$ and $SO_4Cu$ are equimolar. According to a particular embodiment, the process (II) of the invention comprises: a step of forming a solution A comprising the transition metal in the form of a soluble salt of copper (II), CTAB and the water;
- a step of forming a solution B comprising $Na_2S$ and water;
- a step of precipitating the soluble salt of copper (II) by the addition of the solution A to the solution B to form a suspension of nanoparticles of copper (II) sulfide;

According to a particular embodiment, the method (II) of the invention comprises:
- a step of forming a solution A comprising the transition metal in the form of a soluble silver salt (I), CTAB and water;
- a step of forming a solution B comprising $Na_2S$ and water;
- a step of precipitation of the soluble silver salt (I) by the addition of the solution A to the solution B to form a suspension of nanoparticles of silver sulfide (I);

The concentration of $Na_2S$ is the stoichiometric concentration for the formation of the insoluble salt. If the salt is $NO_3Ag$, the molar concentration of $Na_2S$ is half that of $NO_3Ag$ According to a particular embodiment, the method (II) of the invention comprises:
- a step of forming a solution A comprising the transition metal in the form of a soluble salt of gold (III), CTAB and water;
- a step of forming a solution B comprising $Na_2S$ and water;
- a step of precipitating the soluble salt of gold (III) by the addition of solution A to solution B to form a suspension of gold (III) sulfide nanoparticles;

The concentration of $Na_2S$ is the stoichiometric concentration for the formation of the insoluble salt. If the salt is $Cl_3Au$, the molar concentration of $Na_2S$ is 1.5 times that of $Cl_3Au$ The optimum conditions for the preparation of metal sulfide nanoparticles according to the invention can be determined by those skilled in the art, in particular in view of the examples of the present invention.

According to an advantageous embodiment, the invention relates to nanoparticles obtained by the process (II).

EXAMPLES

I) Synthesis of the Complexes

Example 1 SCu Solution

Figure 1:
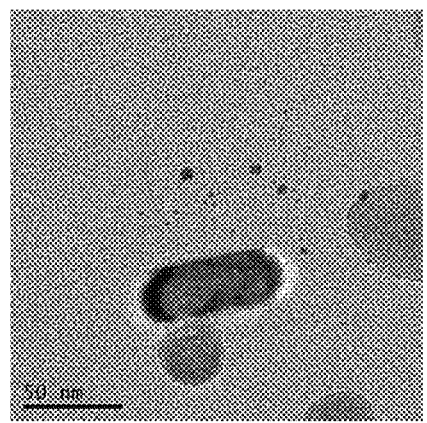
FIG. 1 shows an HR-TEM image of the $SAg_2$ particles according to Example 4.
Figure 2:
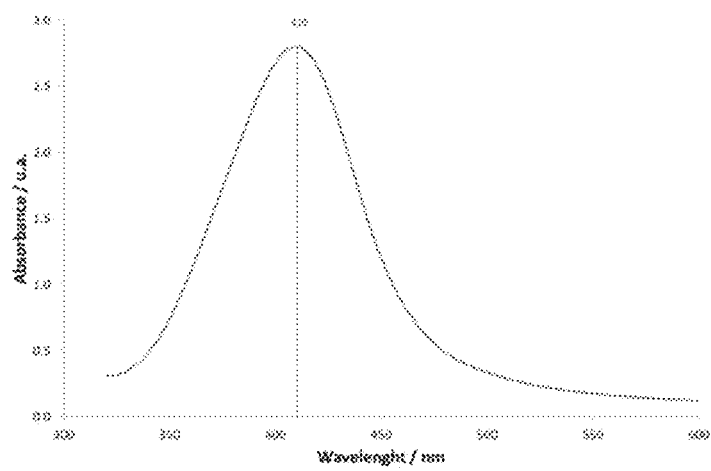
FIG. 2 shows the UV-visible absorption spectrum of an aqueous suspension of silver nanoparticles at a concentration of 0.2 wt % silver according to Example 8B.

Dissolve 126 mg of $SO_4Cu$ in 90 mL of water.
Dissolve 140 mg of $Na_2S$ in 20 mL of water.

Mix the 90 mL of the $SO_4Cu$ solution with 10 mL of the $Na_2S$ solution. A precipitate of 75 mg of SCu is obtained. Separate it by filtration.

Place this precipitate in 100 mL of water in a stirred container.

With constant stirring, drop a very concentrated solution of $NH_3$ into the water very slowly.

The maximum concentration of SCu in water is 0.33 $mg.l^{-1}$ SCu becomes more soluble in aqueous solution in the presence of ammonia. The addition of ammonia to copper sulfide makes it possible to reach an aqueous concentration of at least 0.2 $g.l^{-1}$ in Cu.

Example 2 $SAg_2$ Solution

Dissolve 79 mg of $NO_3Ag$ in 97 mL of water.
Mix the 97 mL of the $NO_3Ag$ solution with 3 mL of the $Na_2S$ solution. A precipitate of 75 mg of $SAg_2$ is obtained. Separate it by filtration.

Place this precipitate in 100 mL of water in a stirred container.

With constant stirring, drop very slowly a concentrated solution of ammonium citrate $(NH_4)_5(C_6H_4O_7)_2H_3$.

The maximum concentration of $SAg_2$ in water is $6.21.10^{-15}$ $g.l^{-1}$. $SAg_2$ becomes more soluble in the presence of citric acid, or a mixture of ammonium citrate and citric acid, or a mixture of ammonium citrate and ammonia, the ammonium citrate being formed by a mixture of citric acid and ammonia. The addition of citric acid, or a mixture of ammonium citrate and citric acid, or a mixture of ammonium citrate and ammonia, to the silver sulfide makes it possible to reach a concentration at least 0.2 $g.l^{-1}$ in Ag.

Example 3 Solution $S_3Au_2$

Dissolve 77 mg of $Cl_3Au$ in 95 mL of water. Mix the 95 mL of the $Cl_3Au$ solution with 5 mL of the $Na_2S$ solution. A precipitate of 62 mg of $S_3Au_2$ is obtained. Separate it by filtration.

Place this precipitate in 100 mL of water in a stirred container.

While stirring constantly, drop a very concentrated solution of potassium dichromate very slowly. The maximum concentration of $Au_2S_3$ in water is undetectable. The aqueous solubility of $Au_2S_3$ is increased in the presence of potassium dichromate, or a mixture of potassium dichromate and ammonia. The addition of potassium dichromate, or a mixture of potassium dichromate and ammonia, to the gold sulfide makes it possible to reach an aqueous concentration of at least 0.2 $g.l^{-1}$ in Au.

II) Synthesis of Metal Sulfide Nanoparticles

Example 4 $SAg_2$ Nanoparticles

Example 4A. $SAg_2$ Nanoparticles

All reagents are used as received, without prior purification.

The water used to prepare the solution is ultra-pure water degassed and stored under Argon.

The reaction takes place under Argon at room temperature (20° C.).

The silver solution is handled in the dark (protection under aluminum).

For the synthesis of 200 mL of 0.2 wt % colloidal solution (2 $g.l^{-1}$) of silver nanoparticles:

For the preparation of solution A, prepare 80 ml of ultrapure water in a flask and dissolve first 1.35 g of cetyltrimethylammonium bromide (CTAB, $3.7.10^{-3}$ mol) in water and then 0.4 g $Ag^+$ in the form of $AgNO_3$ ($2.3.10^{-3}$ mol) and adjust to 100 ml with ultrapure water. Store cold, in the dark.

For the preparation of solution B, prepare 50 mL of ultra-pure water in a flask, dissolve 0.144 g of $Na_2S$ (1.85× 10 −3 mol) and adjust to 100 mL with ultrapure water.

At room temperature, in the dark, under an argon atmosphere and with stirring (600 rpm), add dropwise solution A to solution B. Allow to react for 4 hours. The $SAg_2$ particles are characterized by HR-TEM, FIG. They have a wide size distribution with a majority presence of particles larger than 20 nm. Example 4B. $SAg_2$ nanoparticles, effect of temperature Silver sulfide nanoparticles are synthesized according to Example 4A at 0° C.

There is an insignificant difference in bactericidal activity between nanoparticles obtained at room temperature and those obtained at 0° C. (see table 1 lines R and 0)

Example 4C. $SAg_2$ Nanoparticles, Effect of Surfactant

Silver sulfide nanoparticles are synthesized according to Example 4A, using PEG-600 in place of CTAB.

Example 5 SCu Nanoparticles

Example 5A. SCu Nanoparticles

All reagents are used as received, without prior purification.

The water used to prepare the solution is ultra-pure water degassed and stored under Argon.

The reaction takes place under Argon at room temperature (20° C.).

For the synthesis of 200 mL of 0.2 wt % colloidal solution (2 g.l$^{-1}$) of copper nanoparticles:

For the preparation of solution A, prepare 80 ml of ultra-pure water in a flask and first dissolve 1.35 g of CTAB ($3.7.10^{-3}$ mol) in water and then 0.4 g of Cu2+ in the form of $CuSO_4$ ($2.5.10^{-3}$ mol) and adjust to 100 mL with ultrapure water. Store cold, in the dark.

To prepare solution B, prepare 50 mL of ultra-pure water in a flask, dissolve 0.5 g of $Na_2S$ ($0.64.10^{-3}$ mol) and adjust to 100 mL with ultra-pure water. pure.

At room temperature, in the dark, under an argon atmosphere and with stirring (600 rpm), add dropwise solution A to solution B. Allow to react for 4 hours.

Example 5B. SCu Nanoparticle, Effect of Temperature

Copper sulfide nanoparticles are synthesized according to Example 5A at 0° C. There is no difference in the bactericidal activity between the nanoparticles obtained at ambient temperature and those obtained at 0° C. (see lines Q and T of Table 1)

Example 5C. Nanoparticle SCu, Effect of Surfactant

Copper sulfide nanoparticles are synthesized according to Example 5A, using PEG-600 in place of CTAB.

Example 6 $S_3Au_2$ Nanoparticles

Example 6A. $S_3Au_2$ Nanoparticles

All reagents are used as received, without prior purification.

The water used to prepare the solution is ultra-pure water degassed and stored under Argon.

The reaction takes place under Argon at room temperature (20° C.).

The gold solution is handled in the dark (protection under aluminum).

For the synthesis of 200 mL of 0.2 wt % colloidal solution (2 g.l$^{-1}$) of gold nanoparticles:

For the preparation of solution A, prepare 80 mL of ultrapure water in a flask and first dissolve 1.35 g of CTAB ($3.7.10^{-3}$ mol) in water and then 0.4 g of $Au^{3+}$ in the form of $AuCl_3$ ($1,3.10^{-3}$ mol) and adjust to 100 mL with ultrapure water. Store cold, in the dark.

For the preparation of solution B, prepare 50 mL of ultra-pure water in a flask, dissolve 0.234 g of $Na_2S$ ($0.3.10^{-3}$ mol) and adjust to 100 mL with ultrapure water.

At room temperature, in the dark, under an argon atmosphere and with stirring (600 rpm), add dropwise solution A to solution B. Allow to react for 4 hours.

Example 6B. $S_3Au_2$ Nanoparticles, Effect of Temperature

Gold sulfide nanoparticles are synthesized according to Example 6A at 0° C.

The nanoparticles obtained at room temperature are a little more efficient than those obtained at 0° C. (see Table 1 lines P and S)

III) Synthesis of Transition Metal Nanoparticles

Example 7 How to Synthesize Suspensions of Metallic Nanoparticles in Water?

The metallic nanoparticles in water are generated by the reaction of a salt of the metal and a reagent:
the reagent being an oxidant to obtain nanoparticles of metal oxides;
the reagent being a reducing agent to obtain metal nanoparticles.

In addition, the metal salts must be stabilized in "cages" in order to prevent agglomeration of nanoparticles into larger and more stable particles.

The cages are generally formed with surfactants having a hydrophilic portion and a hydrophobic portion. These cages, in an aqueous medium, are called micelles.

Example 8. Silver Nanoparticles, Ag

Example 8. A Selection of Reagents

The available silver salt (and the most common) is $AgNO_3$. (Aldrich, 99%, M=169.9 g.mol$^{-1}$, assay 63.4% Ag).

The surfactant used is CTAB (cetyltrimethylammonium bromide).

The reducer chosen is glycerol.

The use of glycerol involves the use of a base to enhance its reducing properties. NaOH was used for this purpose to produce a basic solution of glycerol in water. These solutions aim to reduce the $Ag^+$ metal salt by converting glycerol to dihydroxyacetone (DHA).

Example 8.B Synthesis of 200 mL of 0.2 wt % Colloidal Solution (2 g.l$^{-1}$) of Silver Nanoparticles All reagents are used as received, without prior purification. The water used to prepare the solution is ultra-pure water degassed and stored under Argon. The reaction takes place under Argon at room temperature (20° C.). The silver solution is handled in the dark (protection under aluminum). For the preparation of solution A, prepare 80 ml of ultrapure water in a flask and first dissolve 1.35 g of CTAB ($3.7 \times 10^{-3}$ mol) in water and then 0.4 g Ag$^+$ ion as AgNO$_3$ ($2.3.10^{-3}$ mol) and adjust to 100 mL with ultrapure water. Store cold, in the dark.

For the preparation of solution B, prepare 50 mL of ultra-pure water in a flask, dissolve 34 g of glycerol (0.37 mol) and then 8 g of NaOH (0.2 mol) and adjust to 100 mL with ultra-pure water.

At room temperature, in the dark, under an argon atmosphere and with stirring (600 rpm), add dropwise solution A to solution B. Allow to react for 4 hours. At the end of the reaction, adjust the pH to 7 by adding concentrated commercial HCl (24 M). The corresponding volume to be added is from 0.8 to 0.9 ml.

The resulting solution is analyzed by UV-visible spectroscopy and the morphology and size of the particles obtained are analyzed by high-resolution transmission electron microscopy (HR-TEM).

The UV-visible absorption wavelength is specific to the size and quantity of the nanoparticles in suspension. The UV-visible spectroscopic analysis of the colloidal suspension of silver nanoparticles at a concentration of 0.2 wt % is shown in FIG. The solution has no deposit, all the money initially introduced is in colloidal form.

The distribution is mono-modal with a wavelength centered at 410 nm, indicating a nanoparticle size of less than 40 nm. The size of the nanoparticles is then confirmed by HR-TEM microscopy.

Figure 3:
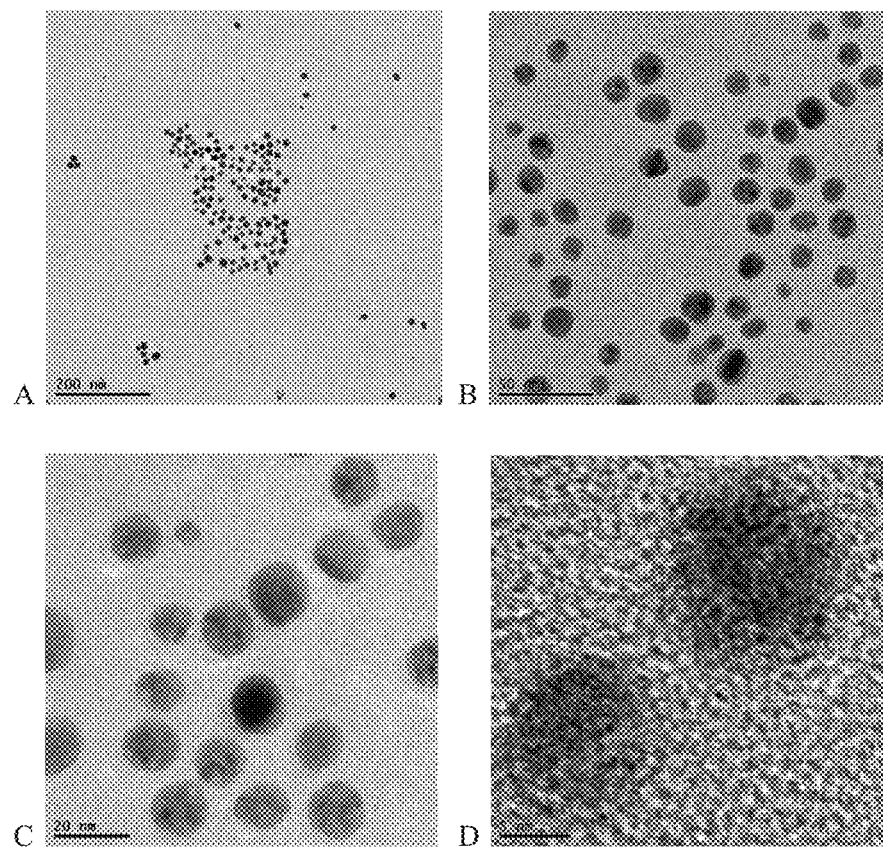
FIG. 3 shows HR-TEM images of the silver particles of Example 8B. A, B, C and D correspond to different size scales.

The images obtained by HR-TEM are presented in FIG. 3, at different scales. The nanoparticles are homogeneous in size, with an average diameter of 15 nm.

Example 8.0 Effect of Reagent Concentration on Nanoparticle Formation

In order to increase the concentration of nanoparticles and reach a concentration of 2 g.l$^{-1}$ (0.2 wt %) in silver, the amount of reagents was increased. However, the total amount of CTAB is not soluble under these conditions and most of it precipitates. The stabilization of silver nanoparticles is no longer assured.

Figure 4:
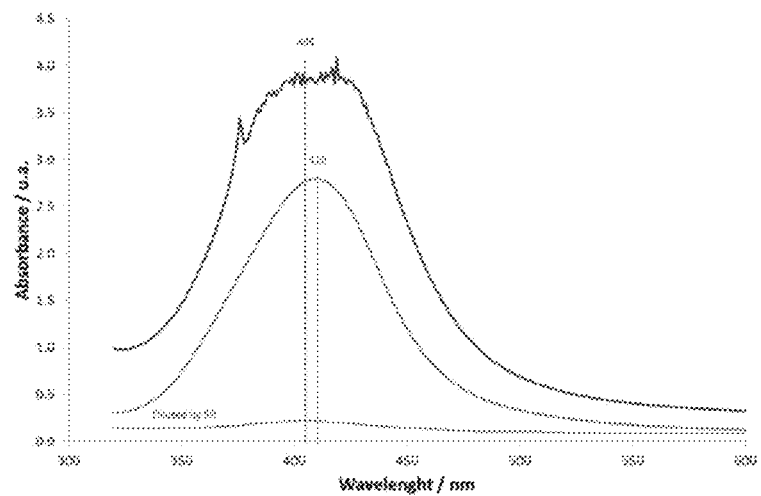
FIG. 4 shows the UV-visible absorption spectrum of the silver nanoparticle solution at a concentration of 0.14 $g.l^{-1}$ (Example 8C) compared to the solution of Example 8B.
Figure 5:
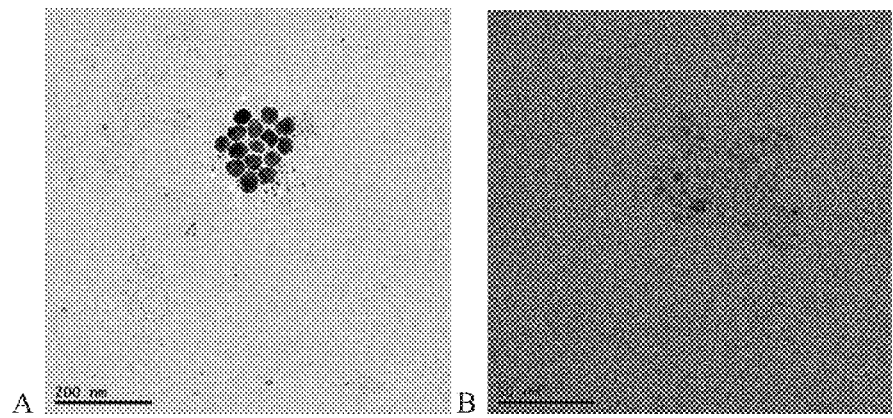
FIG. 5 shows an HR-TEM microscopy image made on the 0.14 $g.l^{-1}$ suspension of Example 8C. A, B, C and D correspond to different size scales.
Figure 5:
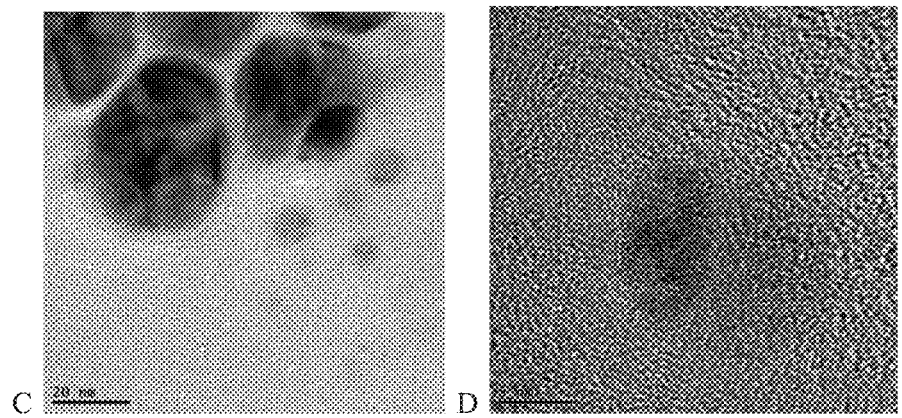

The UV-visible absorption spectrum resulting from a suspension that has been diluted about 50-fold to avoid saturation of the UV spectrum is shown in FIG. 4. It can be deduced from the comparison of this spectrum with the spectrum obtained in Example 8.B that the solution has a silver concentration of 0.14 g.l$^{-1}$.

An HR-TEM microscopy analysis was performed on this suspension diluted to 0.14 g.l$^{-1}$. The distribution is bimodal with nanoparticles having a diameter of about 30 nm and smaller nanoparticles with a diameter of less than 5 nm. This behavior is directly related to a stabilizer defect.

Figure 6:
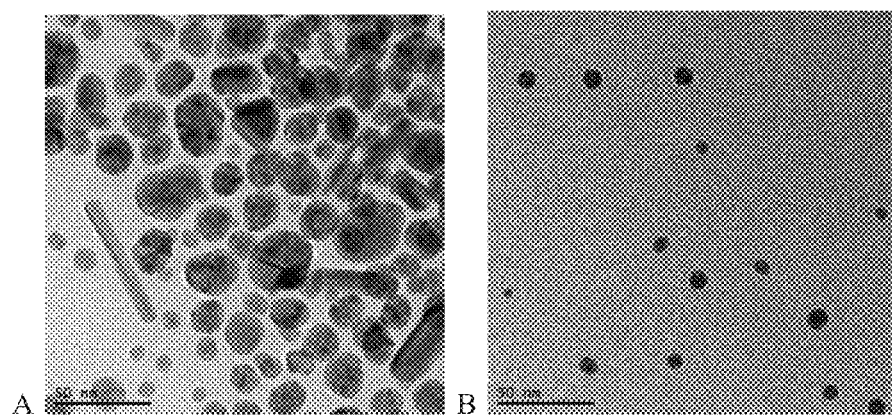
FIG. 6 shows HR-TEM images of the 2 $g.l^{-1}$ solution prepared in Example 8C. A and B correspond to different size scales.

The solution obtained according to the method 8.B but with a concentration of 2 g.l$^{-1}$ in silver, is golden in color. The HR-TEM images of this solution 2 g.l$^{-1}$ (concentrated solution prepared in 8.0 are reported in FIG. 6. The particles obtained are not homogeneous. FIG. 6A illustrates the presence of nanoparticles with an average diameter of 30 nm, these nanoparticles being of various shapes (rods, spheres). Small spherical nanoparticles, whose average diameter is 5 to 10 nm, are also present in the solution, as shown in FIG. 6B.

Example 8.D Effect of the Concentration eh Silver on the Size of the Silver Nanoparticles The silver concentration is obtained by vacuum distillation of water (p=15 mbar at 20° C.) of the initial colloidal solution prepared according to Example 8.B.

A solution of silver nanoparticles with a concentration of 0.2 g l$^{-1}$ and smaller than 15 nm (Example 8.B) is concentrated by vacuum distillation of water to give a silver concentration of 2 g.l$^{-1}$. The resulting solution is cloudy and golden.

Figure 7:
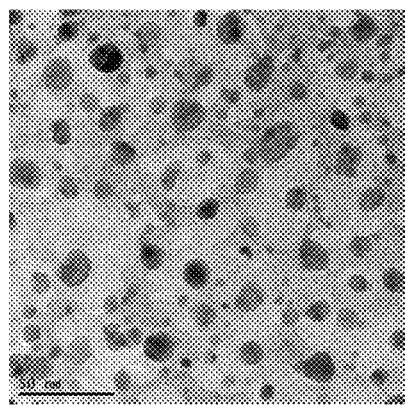
FIG. 7 shows an HR-TEM image of the colloidal solution of silver nanoparticles at 2 $g.l^{-1}$ obtained after vacuum distillation of the water of a suspension at 0.2 $g.l^{-1}$, according to Example 8D.

The images obtained by HR-TEM of this new suspension are shown in FIG. 7.

Figure 8:
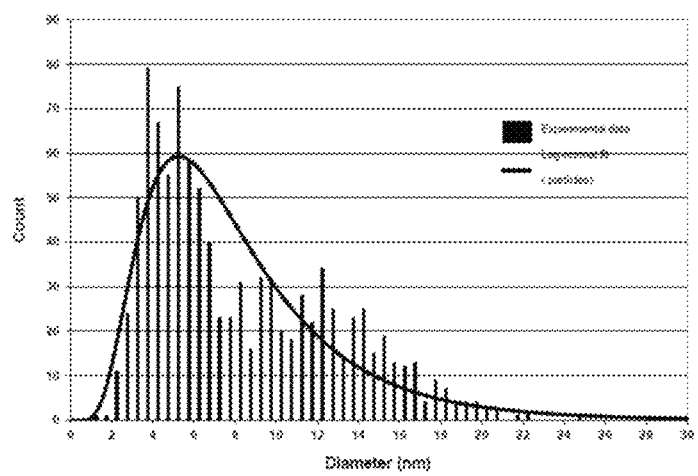
FIG. 8 shows a histogram of the size distribution of the silver nanoparticles in a concentrated suspension at 2 $g.l^{-1}$ according to Example 8D. The counting of nanoparticles and the determination of the size of each of them are made on a microscope slide.

The generally spherical nanoparticles have a broad size distribution (5 to 20 nm), FIGS. 7 and 8.

It should be noted, however, that CTAB precipitates upon removal of water.

Example 8.E Effect of the Nature of the Surfactant on the Formation of Nanoparticles A nanoparticle solution is produced according to Example 8.B using octyltrimethylammonium bromide (OTAB) in place of cetyltrimethylammonium bromide (CTAB).

The resulting solution is green. A hypsochromic displacement of the wavelength of the absorption maximum of this solution is indeed observed during the analysis by UV-visible absorption spectroscopy. Plasmon generated on the surface is therefore more energetic than when the nanoparticles are formed in the presence of CTAB.

Figure 9:
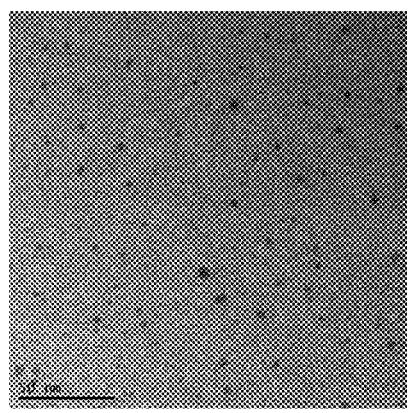
FIG. 9 shows an HR-TEM image of silver nanoparticles obtained according to method 8. B but in the presence of octyltrimethylammonium bromide (OTAB) according to Example 8E.
Figure 10:
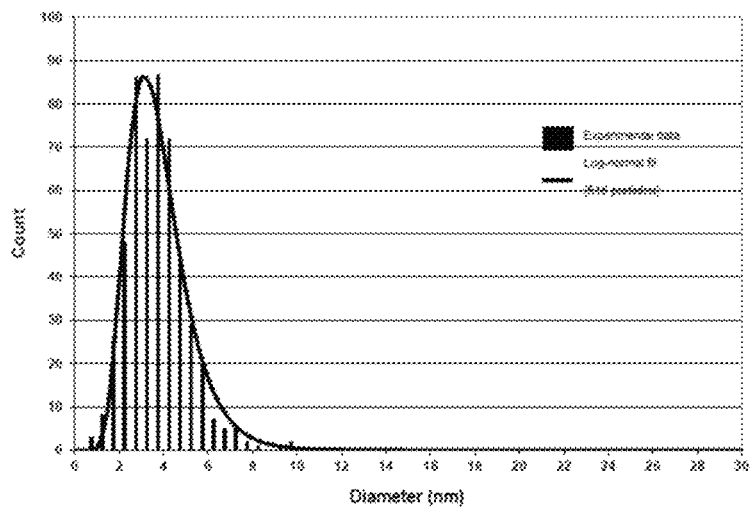
FIG. 10 shows a histogram of the size distribution of the silver nanoparticles in a concentrated suspension at 0.2 $g.l^{-1}$ prepared in the presence of octyltrimethylammonium bromide (OTAB) according to Example 8E. The counting of nanoparticles and the determination of the size of each of them are made on a microscope slide.

FIG. 9 represents an image obtained by HR-TEM microscopy of the green solution. The size of the nanoparticles is very small, with a diameter of less than 5 nm. An average diameter of 3.7 nm is determined by an analysis of the particle size distribution of the solution (FIG. 10).

The counting of nanoparticles and the determination of the size of each of them are made on a microscope slide. 100 nanoparticles are needed so that the determined size distribution is representative of the entire population of the starting colloidal solution. Then the distribution is adjusted by a log-normal law.

Example 8F. Effect of the Nature of the Surfactant on the Formation of Nanoparticles A nanoparticle solution is produced according to Example 8.B using PEG-dithiol in place of cetyltrimethylammonium bromide (CTAB).

Example 9. Gold Nanoparticles, Au

All reagents are used as received, without prior purification. The water used to prepare the solution is ultra-pure water degassed and stored under Argon. The reaction takes place under Argon at room temperature (20° C.).

200 mL of 0.2 wt % colloidal solution (2 g./l) in gold nanoparticles are synthesized by following the following steps:

For the preparation of solution A, prepare 80 mL of ultra-pure water in a flask and first dissolve 0.73 g of CTAB ($2.0 \cdot 10^{-3}$ mol) in water and then 0.4 g $Au^{3+}$ in the form of $AuCl_3$ ($1.3 \cdot 10^{-3}$ mol) and adjust to 100mL with ultrapure water. Store cold.

For the preparation of solution B, prepare 50 mL of ultra-pure water in a flask, dissolve 0.2 mol of glycerol (18.4 g) then 0.2 mol of NaOH (8 g) and adjust to 100 mL with ultra-pure water. At room temperature, under an argon atmosphere and with stirring (600 rpm), add dropwise solution A to solution B. Allow to react for 4 hours.

Figure 11:
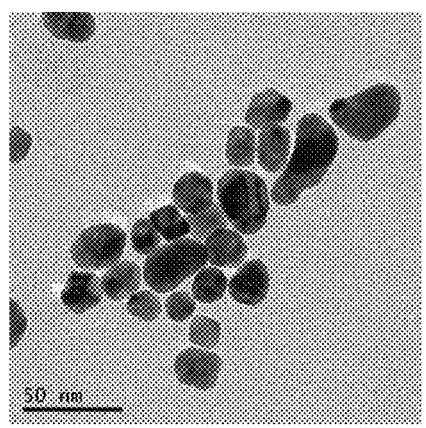
FIG. 11 shows an HR-TEM image of the gold nanoparticle suspension according to Example 9.

At the end of the reaction, adjust the pH to 7 by adding concentrated commercial HCl (24 M). The corresponding volume to be added is from 0.8 to 0.9 mL FIG. 11 represents an HR-TEM image of the obtained gold nanoparticles. Their sizes vary between 10 and 30 nm.

Example 10 Copper Nanoparticles, Cu

Example 10A. Synthesis of Copper Nanoparticles, Cu Copper Nanoparticles Are Synthesized According to the Protocol Described in Example 8B:

All reagents are used as received, without prior purification. The water used to prepare the solution is ultra-pure water degassed and stored under Argon. The reaction takes place under Argon at room temperature (20° C.).

For the preparation of solution A, prepare 80 mL of ultrapure water in a flask and first dissolve 1.35 g of CTAB ($3.7 \cdot 10^{-3}$ mol) in water and then 0.4 g of $Cu^{2+}$ in the form of $Cu(NO_3)_2$ (Molar mass: 187.56 g/mol: 0.75 g Cu $(NO_3)_2 = 4.10^{-3}$ mol) and adjust to 100 mL with ultra-pure water. Store cold, in the dark.

To prepare solution B, prepare 50 mL of ultra-pure water in a flask, dissolve 0.37 mol of glycerol (34 g) and then 8 g of NaOH (0.2 mol) and make up to 100 mL with ultra-pure water.

At room temperature, in the dark, under an argon atmosphere and with stirring (600 rpm), add dropwise solution A to solution B. Allow to react for 4 hours.

At the end of the reaction, adjust the pH to 7 by adding concentrated commercial HCl (24 M). The corresponding volume to be added is from 0.8 to 0.9 mL.

Figure 12:
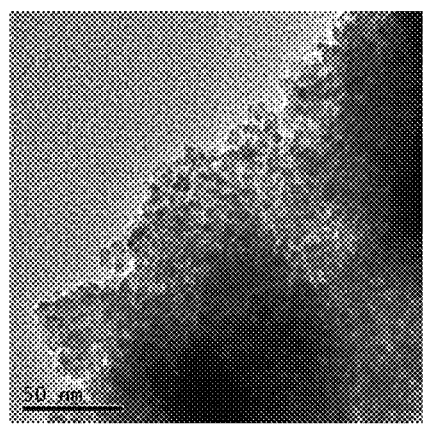
FIG. 12 shows an HR-TEM image of the colloidal solution comprising the copper nanoparticles according to Example 10.

FIG. 12 represents an HR-TEM image of the copper nanoparticles included in the colloidal suspension thus obtained.

Figure 13:
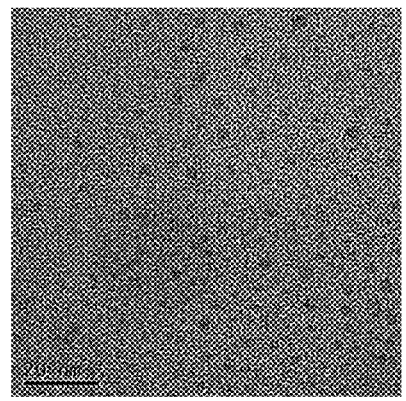
FIG. 13 shows an HR-TEM image of the colloidal solution comprising the copper nanoparticles according to Example 10.

Clusters of small particles are observed showing that the surfactant does not allow complete stabilization of the copper nanoparticles. Some isolated nanoparticles are also present as illustrated in FIG. 13. These nanoparticles are homogeneous and small, with a diameter of about 2 nm.

Example 10B. Effect of the nature of surfactant on the formation of copper nanoparticles A nanoparticle solution is made according to Example 10A using PEG-600 in place of cetyltrimethylammonium bromide (CTAB).

Example 11 Attempt to Prepare Sulfur Nanoparticles

According to the procedure 8. B from $Na_2S$ and PEG-600 as surfactant: a 0.2 g/l colloidal solution in sulfur was obtained.

Figure 14:
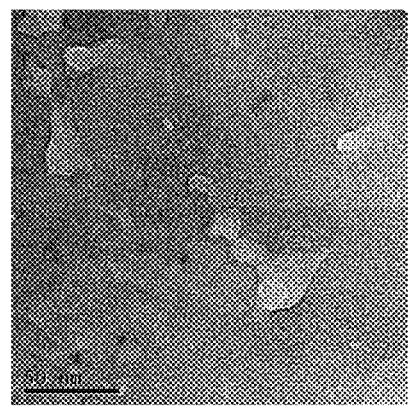
FIG. 14 represents an HR-TEM image of the colloidal solution comprising the sulfur nanoparticles according to Example 11.

Objects homogeneous in size and about 5 nm in diameter but difficult to observe by HR-TEM microscopy due to low contrast (FIG. 14) could be observed. These objects because of their size were called sulfur nanoparticles.

IV) Biological Results

Example 12. MIC Test on MRSA and MSSA Bacteria: Materials and Methods

The bacteria MRSA (Meticillin Resistant *Staphylococcus aureus*, ATCC 43300) and MSSA (Meticillin Sensitive *Staphylococcus aureus*, ATCC 29213) were incubated on TSA 24 h at 37° C. The standardization of the bacteria was carried out by producing a farland 0.5 mc with fresh colonies, representing $1.5 \cdot 10^7$ $CFU.ml^{-1}$ then the bacterial suspension was diluted $\frac{1}{100}^{th}$ in a Mueller Hinton (MH) medium (sigma. 90922-500G) in order to obtain a final bacterial concentration (spf) corresponding to $1.5 \cdot 10^5$ CFU/ml.

Each particle test was performed on a line of a 96-well round bottom plate (ref.353077) in duplicate. 50 μL of MH medium were deposited in the wells. 50 μL of the pure particle were deposited in the first column (column 1) of the plate and successive dilutions of reason 2 were performed by taking 50 μl of each column redeposited in the next column to the last column (column 12). The 50 μl of the last column were discarded. Then 50 μl of the bacterial suspension (spf) was deposited in each well representing a final bacterial concentration per well of $0.75 \cdot 10^5$ $CFU.ml^{-1}$. The final concentration of the particle in the first well (column 1) represents a final ¼ dilution with respect to its initial concentration.

Two negative controls were performed with pure MH, and with 50 μL of MH and 50 μL of pure particle to verify that there was no contamination. A positive control was performed with 50 μL of MH and 50 μL of the bacterial suspension (spf).

The plate was incubated for 24 h at 37° C. in a humid chamber. As this method is the reference method for determining the MIC of a particle, a control of the MIC for oxacillin was performed on these same strains MSSA and MRSA.

Example 13 MIC Test on MRSA and MSSA Bacteria: Results

The first bacteria-free cupule is determined to be the Minimum Inhibitory Concentration (MIC) of the particle.

TABLE 1

Minimal Inhibitory Concentration (MIC) assay of aqueous solutions obtained by use of the present invention on MRSA and MSSA bacteria. The nanoparticles of Ag(O) (according to Example 8), of Cu(O) (according to Example 10) and of Au(O) (according to Example 9) are denoted Ag, Cu and Au, respectively, and the silver sulfide nanoparticles (according to Example 4), copper sulfide (according to Example 5) and gold sulfide (according to Example 6) are respectively denoted $Ag_2S$, CuS and $Au_2S_3$. $CuSO_4$ relates to a solution of soluble copper salt in the meaning of the invention, that is to say a solution of copper sulfate in water. S represents an aqueous solution of sulfur nanoparticles prepared according to Example 11.

| Number | Particle/quantity | MICMSSA (g/l) | MIC MRSA (g/l) |
|---|---|---|---|
| Control | Oxacilline | $2.5 \cdot 10^{-4}$ | 0.256 |
| A | Ag (Example 8B) | $7.81 \cdot 10^{-4}$ | $7.81 \cdot 10^{-4}$ |
| B | Ag (Example 8F) | 0.05 | 0.05 |
| D | S (Example 11) | 0.05 | 0.05 |
| F | Cu 0.2 g/L (Example 10A) | $4.88 \cdot 10^{-5}$ | $9.71 \cdot 10^{-5}$ |
| H | Au (Example 9) | $4.88 \cdot 10^{-5}$ | $3.9 \cdot 10^{-4}$ |
| K | Cu (Example 10B) | 0.025 | 0.05 |
| L | $Ag_2S$ PEG-600 (Example 4C) | 0.0125 | Not done |

TABLE 1-continued

Minimal Inhibitory Concentration (MIC) assay of aqueous solutions obtained by use of the present invention on MRSA and MSSA bacteria. The nanoparticles of Ag(O) (according to Example 8), of Cu(O) (according to Example 10) and of Au(O) (according to Example 9) are denoted Ag, Cu and Au, respectively, and the silver sulfide nanoparticles (according to Example 4), copper sulfide (according to Example 5) and gold sulfide (according to Example 6) are respectively denoted $Ag_2S$, CuS and $Au_2S_3$. $CuSO_4$ relates to a solution of soluble copper salt in the meaning of the invention, that is to say a solution of copper sulfate in water. S represents an aqueous solution of sulfur nanoparticles prepared according to Example 11.

| Number | Particle/quantity | MICMSSA (g/l) | MIC MRSA (g/l) |
|---|---|---|---|
| N | CuS PEG-600 (Example 5C) | 0.0125 | Not done |
| O | $Ag_2S$ (Example 4A) | $1.95 \cdot 10^{-4}$ | $3.9 \cdot 10^{-4}$ |
| P | $Au_2S_3$ (Example 6A) | $2.44 \cdot 10^{-5}$ | $4.88 \cdot 10^{-5}$ |
| Q | CuS (Example 5A) | $9.71 \cdot 10^{-5}$ | $9.71 \cdot 10^{-5}$ |
| R | $Ag_2S$ (Example 4B) | $1.95 \cdot 10^{-4}$ | $1.95 \cdot 10^{-4}$ |
| S | $Au_2S_3$ (Example 6B) | $4.88 \cdot 10^{-5}$ | $9.71 \cdot 10^{-5}$ |
| T | CuS (Example 5B) | $9.71 \cdot 10^{-5}$ | $9.71 \cdot 10^{-5}$ |
| V | $CuSO_4$ | 0.078 | 0.078-0.157 |
| A + D | ⅛ D + ⅞ A | $7.81 \cdot 10^{-4}$ | $7.81 \cdot 10^{-4}$ |
| H + D | ⅛ D + ⅞ H | $9.71 \cdot 10^{-5}$ | $9.71 \cdot 10^{-5}$ |
| F + D | ⅛ D + ⅞ F | $4.88 \cdot 10^{-5}$ | $1.95 \cdot 10^{-4}$ |
| D + A + H | ⅛ D + 3, ⅝ A + 3, ⅝ H | $9.71 \cdot 10^{-5}$ | $1.95 \cdot 10^{-4}$ |
| D + A + F | ⅛ D + 3, ⅝ A + 3, ⅝ F | $9.71 \cdot 10^{-5}$ | $9.71 \cdot 10^{-5}$ |
| D + H + F | ⅛ D + 3, ⅝ H + 3, ⅝ F | $4.88 \cdot 10^{-5}$ | $9.71 \cdot 10^{-5}$ |
| D + A + H + F | ⅛ D + ⅖ A + ⅖ H + ⅜ F | $4.88 \cdot 10^{-5}$ | $9.71 \cdot 10^{-5}$ |
| D + K | ⅛ D + ⅞ K | 0.025 | 0.05 |
| O + P | ½ O + ½ P | $9.71 \cdot 10^{-5}$ | $9.71 \cdot 10^{-5}$ |
| P + Q | ½ P + ½ Q | $4.88 \cdot 10^{-5}$ | $9.71 \cdot 10^{-5}$ |
| O + Q | 1/2 O + ½ Q | $7.81 \cdot 10^{-4}$ | $1.95 \cdot 10^{-4}$ |

The control represents the expected MIC for these strains. The MICs of the different particles show a bactericidal effect for most of the MSSA and MRSA strains at different concentrations.

In addition, the nanoparticles of the invention are all better inhibitors of MRSA than oxacillin. Oxacillin, used herein as a reference, is an example of an active substance used in case of infection with Staphylococci. Among the compounds of the invention, the copper nanoparticles, the gold sulfide nanoparticles and the copper sulfide nanoparticles have the best inhibition rates, both of the MSSA bacteria and of the MRSA bacteria.

Example 14. MIC Test on Gram-positive/Negative Bacteria and Yeasts

The nanoparticle in question is copper sulfide surfactant with CTAB, synthesized according to Example 5, the copper source being copper nitrate, $Cu(NO_3)_2$, and not copper sulphate. The tests are carried out according to the method described in Example 12

The activities are measured by the MIC (Minimum Inhibitory Concentration), the index generally used, expressed here in mg per liter. One mg per liter represents a ppm:

| | | |
|---|---|---|
| Gram-positive bacteria | *Staphylococcus Aureus* | 0.&5 |
| | *Propionibacterium Acnes* | 0.07 |
| Gram-negative bacteria | *Pseudomonas Aeruginosa* | 1.2 |
| Yeast | *Candida Albicans* | 0.32 |

These nanoparticles are active in particular on the bacterium that produces acne: the minimum inhibitory concentration against Propionibacterium acnes is 0.07 mg per liter.

Copper sulfide nanoparticles are not only active, but are also very well tolerated, in particular since the concentration in an anti-acne cream is low: in the order of ppm.

Example 15

It should be noted that in all of the above examples involving CTAB, it can be reduced to a molar concentration equal to 0.5 times that of the metal.

Two suspensions of copper sulfide nanoparticles with a CTAB/Cu ratio of 1 and 0.2 respectively were prepared according to the protocol of Example 5 and using the starting materials below.

| | |
|---|---|
| $CuSO_4 \cdot 5H_2O$ | Molar mass: 249.69 g |
| $Na_2S \cdot 9H_2O$ | Molar mass: 240.18 g |
| CTAB | Molar mass: 364.45 g |

Solution at 2 g/l Cu (Molar mass: 63.55 g)
0.2 g per 100 ml corresponding to 3.15 mmol of $CuSO_4 \cdot 5H_2O$ Two suspensions of CuS in 100 ml of water were prepared at room temperature.

Suspension 1 CTAB/Cu ratio=1 in 100 ml
3.15 mmol $CuSO_4 \cdot 5H_2O$ that is m=0.786 g
3.15 mmol $Na_2S \cdot 9H_2O$ that is m=0.757 g
3.15 mmol of CTAB that is m=1.148 g
These suspensions are stable after 48 hours at room temperature Suspension 2 CTAB/Cu ratio=0.5
3.15 mmol $CuSO_4 \cdot 5H_2O$ that is m=0.786 g
3.15 mmol $Na_2S \cdot 9H_2O$ that is m=0.757 g
0.64 mmol of CTAB that is m=0.230 g
These suspensions are stable after 48 hours at room temperature

Example 16

The tests on CuS at 1 of CTAB (suspension 2 of Example 15) were made by Ideatest Group.

The bacterium tested is *Propionibacterium acnes*, responsible for acne.

The results are as follows

The lethal concentration is 1 mg/l (one part per million)

There are two other measures, also determined by Ideatest Group. The current measure in Europe is the 4 log concentration (which divides the bacterial population by 10 000) in five minutes. This is achieved for *Propionibacterium acnes* with 1 mg/l.

The standard AFNOR EN 1276, for medical use, much more rigid, is 5 log in five minutes (It divides the bacterial population by 100 000). This is achieved for *Propionibacterium acnes* with 2 mg/l.

A tolerance check was also done by Ideatest Group. Europe now prohibits animal testing and men in this area, laboratories have developed a new method. It involves culturing human skin cells, assembling them in layers to form a "reconstructed skin" and testing on this reconstructed skin.

These tests were made with a concentration of 20 mg/l to have a very wide margin of safety. Unlike all anti-acne agents currently on the market, the nanoparticle of the invention produces no irritation.

Other tests were made with CuS at 10 CTAB, (Example 5) in inhibitory concentration: they gave the following results, in mg.l$^{-1}$. 1 mg.l$^{-1}$ corresponds to one ppm, part per million:

| | | |
|---|---|---|
| Gram-positive bacteria | Staphylococcus Aureus | 0.15 |
| | Propionibacterium Acnes | 0.07 |
| Gram-negative bacteria | Escherichia coli | 1.2 |
| | Pseudomonas Aeruginosa | |
| Yeasts | Candida Albicans | 0.32 |

These results cover all the families of germs, gram-positive, gram-negative and fungi in particular yeasts. They are excellent.

Example 17 Composition

Anti-acne cream, 80% water 20% oil, containing 2 ppm SCu prepared with CTAB as surfactant, the molar concentration ratio of CTAB/Cu was 0.2, made at room temperature.

Example 18 Tests of CuS at 1.15 of CTAB with Respect to Staphylococcus aureus

The measurements on CuS at 1, 15 of CTAB were carried out by the CIRI:
Hospices Civils de Lyon—International Center for Research in Infectiology (CIRI)
Croix-Rousse Hospital
Center of Northern Biology—Laboratory of Bacteriology—Bat O.
103 Great Rue de la Croix Rousse, 69004 LYON, France
The bacterium tested is Staphylococus aureus.
The results are as follows:
The CIRI sought the MIC, Minimal Inhibitory Concentration
On the one hand on MRSA, Meticillin Resistant Staphylococcus aureus
On the other hand on the MSSA, Meticillin Sensitive Staphylococcus aureus
In both cases the MIC was the same: 0.1 mg/l Example 19 Tests of CuS at 1.15 of CTAB with Respect to the Propionibacterium acnes Bacteria The CuS tests at 1.15 of CTAB were performed by the Ideatest Group (Idea Lab, Montesquieu Technopole 5, rue Jacques Monod CS 60077 33652 MARTILLAC CEDEX).
The bacterium tested is Propionibacterium acnes, responsible for acne.
The results are as follows:
The product was tested at concentrations: 0.07, 0.25, 0.5, 1 and 2 mg/l. The monitoring was carried out on the 5 minutes, 24 h and 6 days.
The microorganism tested was removed from freezing (−80° C.) and was twice plated on appropriate medium (TSA: Tryptic Soy Agar). This medium was incubated at 36° C. (±2.5° C.) for 6 days in anaerobic jar in the presence of anaerocult (Merck), P. acnes requiring anaerobic conditions for growth.
The suspension to be tested was prepared extemporaneously in sterile physiological water from the culture on agar medium. The density thus obtained was adjusted by measuring the OD at 620 nm; it should be around $10^8$ cells/ml.
The microorganism to be tested was placed extemporaneously in a liquid medium with a double concentration favorable for its growth (TSB: Tryptic Soy Broth), then immediately inoculated into the product at a final density of between $10^5$ and $10^6$ Forming Unit colonies/ml. More specifically, the contact between the microbial preparation and the test product was made by volume-to-volume addition in a sterile glass vial.
After the 5 min sampling, the anaerobic incubations of the P. acnes preparations were conducted in a thermostatically controlled chamber for 24 hours and 6 days.
At the end of the incubation periods, counts were made in TSA medium, after dilution-neutralization to LT100 over appropriate dilution ranges. The anaerobic incubations of the seeded boxes were then conducted in thermostatically controlled enclosures for 6 days.
The bactericidal activity of the products is evaluated by comparing the densities obtained at the final time (Tf) with those noted at the initial time (TO). The bactericidal potential is estimated from the reduction obtained. It must be greater than 4 log for bacteria.
The bacteriostatic activity of the products is appreciated by the possible decrease in the growth of microbial germs between control (Tef) and test product (Tf).
The following table presents the densities obtained at:
Initial time (TO), the densities being the same for the control and the tests and being in this case $5.0.10^5$ CFU/ml.
Follow-up time for the control (control) and the tests (0.07, 0.25, 0.5, 1 and 2 mg/l).
The results are expressed in CFU/ml.

| | Control | 0.07 | 0.25 | 0.5 | 1 | 2 |
|---|---|---|---|---|---|---|
| T 5 min | 5.0.105 | 9.3.104 | 1.0.105 | 1.2.105 | 1.0.102 | <10 |
| T 24 h | 7.0.105 | 3.9.105 | 3.7.105 | 7.4.104 | <10 | <10 |
| T 6 d | 3.3.106 | 6.9.105 | 9.0.105 | 1.8.104 | <10 | <10 |

The log deductions obtained at each of the times are then calculated with reference to the density TO:

| | Control | 0.07 | 0.25 | 0.5 | 1 | 2 |
|---|---|---|---|---|---|---|
| T 5 min | 0.0 | 0.7 | 0.7 | 0.6 | 3.7 | 4.7 |
| T 24 h | −0.1 | 0.1 | 0.1 | 0.8 | 4.7 | 4.7 |
| T 6 jd | −0.8 | −0.1 | −0.3 | 1.4 | 4.7 | 4.7 |

On the basis of the study carried out, the test product exhibited a bactericidal activity at a concentration of 1 mg/l.

Example 20 Tests of CuS at 1.15 of CTAB with Respect to the Bacterium Acinetobacter baumannii The CuS tests at 1.15 of CTAB were performed by the Microbiological Safety Unit of the Pasteur Institute of Lille (1 rue du Professeur Calmette PO Box 245-59019 LILLE Cedex).
The bacterium tested is Acinetobacter baumannii resistant to penicillins, cephalosporins, carbapenems, quinolones, aminoglycosides (gentamycin).
The results are as follows:
A series of successive dilutions to ½ of the product was carried out. Each dilution was brought into contact with the bacterial suspension of Acinetobacter baumannii (BAA 1792 strain resistant to Penicillins, cephalosporins, carbapenems, quinolones, Aminoglycosides (gentamycin)) and incubated at 37° C. After 24 hours, the tubes with a disorder indicate bacterial growth; the lowest concentration of product for which no disorder is observed is the minimum inhibitory concentration (MIC).

The contents of each tube with no disturbance was then deposited on nutrient agar and incubated at 37° C. After 24 hours, the agars on which no colony is observed indicate that the tube no longer contained culturable bacterium. The lowest concentration of product for which no colony is observed is the minimum bactericidal concentration (MBC).

The MIC of the product with respect to *Acinetobacter baumannii* has been estimated at 4.8 mg/l for concentrations equal to or greater than this value, bacterial multiplication is inhibited (bacteriostatic effect).

The MBC was estimated at 19.2 mg/l for product concentrations greater than or equal to this value, no residual bacterial population appears on agar (bactericidal effect). The CMB was therefore selected as the value to be tested in standard NF EN 1276, as well as a higher concentration (30 mg/l) and a lower estimated non-bactericidal concentration (0.3 mg/l).

Example 21 Tests of CuS at 1.15 of CTAB with Respect to Yeast *Candida albicans*

The CuS tests at 1.15 of CTAB were performed by the Microbiological Safety Unit of the Pasteur Institute of Lille (1 rue du Professeur Calmette PO Box 245-59019 LILLE Cedex).

Yeast tested is Voriconazole-resistant *Candida albicans*, Itraconazole, Fluconazole, Anidulafungin The results are as follows:

The procedure used for the determination of the MICs and CMLs is identical to that described in Example 19.

The MIC of the product against *Candida albicans* has been estimated at 4.8 mg/l for concentrations equal to or greater than this value, microbial growth is inhibited (growth inhibitory effect).

CML was estimated at 9.6 mg/l for product concentrations greater than or equal to this value, no residual microbial population appears on agar (microbicidal effect).

The CML was therefore selected as the value to be tested in the NF EN 1650 standard, as well as a higher concentration (20 mg/l) and a lower estimated non-microbicidal concentration (0.3 mg/l).

Example 22 Tests of CuS at 1.15 of CTAB with Respect to the Bacterium *Escherichia coli*

The CuS tests at 1.15 of CTAB were performed by the Microbiological Safety Unit of the Pasteur Institute of Lille (1 rue du Professor Calmette BP 245-59019 LILLE Cedex).

The bacterium tested is *Escherichia coli* producing extended-spectrum beta-lactamase (ESBL), carbapenem-resistant The results are as follows:

The procedure used for the determination of the MICs and CMLs is identical to that described in Example 19. The MIC of the product with respect to *Escherichia coli* was estimated at 9.6 mg/l for concentrations equal to or greater than this value, the bacterial multiplication is inhibited (bacteriostatic effect).

The MBC was estimated at 76.8 mg/l for product concentrations greater than or equal to this value, no residual bacterial population appears on agar (bactericidal effect).

Example 23 Tests for the Safety of CuS at 1.15 of CTAB with Respect to the Skin The CuS tests at 1.15 of CTAB were performed by the Ideatest Group (Idea Lab, Montesquieu Technopole 5, rue Jacques Monod CS 60077 33652 MARTILLAC CEDEX).

The test consisted of the study of in vitro skin irritation of the reconstructed human epidermis sample (SkinEthic model) according to the OECD guideline 439

The sample was tested at a concentration of 20 mg/m L.

The results are as follows:

The inserts (filter+epidermis) were gently peeled off the agar and if necessary the underside of the inert was wiped on absorbent paper to avoid leaving agar on the polycarbonate filter. The inserts were then placed in wells (6-well culture plate) previously filled with 1 ml of growth medium at room temperature (the absence of bubbles was verified). The cultures were incubated at 37° C., 5% $CO_2$ overnight.

16 µL±0.5 µL of sample to be tested were deposited using a positive displacement micropipette on the surface of the tissues and a 7.5 mm diameter nylon disc was gently applied to the surface of the epidermis. using tongs.

The epidermis were incubated in 0.3 mL of maintenance medium (24-well plate) at room temperature for 42 minutes±1 minute.

The nylon discs were removed and the epidermis was rinsed with 25 mL of PBS per epidermis (25 times 1 mL using a dispenser).

The epidermis was incubated in 2 mL of 6-well plate growth medium at 37° C., 5% $CO_2$ for 42 hours±1 hour (no bubbles were verified). At the end of the incubation period, the plates were stirred for about 2 minutes at 300 rotations per minute to homogenize the mediators or enzymes released into the culture medium.

The culture medium was removed and frozen at −20° C.±5° C. for the optional assay of mediators or enzymes.

All the epidermis were incubated in 0.3 mL of maintenance medium at 1 mg/mL MTT in 24-well plate.

After 3 hours±5 minutes of incubation at 37° C., 5% $CO_2$, the outside of the inserts was rinsed with 2 ml of PBS. The extraction was carried out by placing the epidermis in wells filled with 0.8 ml of isopropanol and then covered with 0.7 ml of isopropanol for 2 hours±5 minutes with gentle stirring at room temperature. Plates were protected by an adhesive film or parafilm to prevent evaporation. The epidermis was pierced and removed from the wells. The extraction solution was homogenized by successive pipetting and the absorbance was measured in triplicate on 200 µl of 96-well plate extract.

Absorbances were measured at 540 nm against a blank consisting of isopropanol.

The result is expressed as a percentage of viability compared to the negative control.

The irritant potential of the tested element has been determined in accordance with the CLP (European Regulation on the Classification, Labeling and Packaging of Substances and Mixtures) and the United Nations Globally Harmonized System of Classification (GHS) Regulations. and Labeling of Chemicals).

The element tested is considered to be skin irritant (Category 2), if the average relative viability, after 42 minutes of exposure and 42 hours of incubation, is less than or equal to 50% of the negative control.

The tested element is considered non-irritant for the skin (no category), if the average relative viability after 42 minutes of exposure and 42 hours of incubation is 50% of the negative control.

The average viability observed for the sample tested is 88.5%, which is therefore non-irritating.

Example 24 Protocol for Synthesis of Nanoparticles Having a Structure Comprising a Core Containing a Transition Metal, Surrounded by a Surfactant Shell A solution A is formed of:

100 this distilled water 0.4 gr $Cu_{++}$, either in the form of $SO_4Cu$ or $(NO_3)_2Cu$. Take care that these two products are delivered in hydrated form with a number of water molecules per variable Cu depending on the suppliers. It must be taken into account so that there is 0.4 gr Cu++

0,46 CTAB gr

Solution B is formed of 100 this distilled water 0.49 gr of $Na_2S$. Take care that $Na_2S$ can be delivered in a hydrated form with a varying number of $Na_2S$ water molecules depending on the supplier. This must be taken into account so that there is 0.49 gr of $Na_2S$.

Drop solution B into solution A in one hour, stirring constantly solution A.

The whole synthesis is done at ambient temperature.

Example 25 Replacement of CTAB by Other Surfactants

Principle:

Bromine CTAB is replaced by another acid (e.g. nitric, sulfuric, acetic, amino, . . . ).

Synthesis protocol:

In a CTAB solution pour the stoichiometric amount of silver powder. Silver bromide precipitates. It is removed by filtration. There remains a solution of CTA OH.

The stoichiometric amount of an acid (eg nitric, sulfuric, acetic, amino, etc.) is poured into this solution.

The CTAX formed, where X is the acid used, is then used as the CTAB to produce transition metal nanoparticles, in particular SCu.

Example 26 Comparison of Golden Staphylococcal Activity of Different Metals and

| | MIC (Minimal Inhibitory Concentration) in PPB | |
|---|---|---|
| Tested sample | MRSA (Meticillin Resistant Staphylococcus Aureus) | MSSA (Meticillin Sensible Staphylococcus Aureus) |
| Ag | 800 | 800 |
| SAg, at r.t. | 200 | 50 |
| SAg, 0° C. | 200 | 200 |
| Au | 400 | 50 |
| SAu, at r.t. | 50 | 25 |
| SAu, 0° C. | 100 | 50 |
| Cu | 100 | 50 |
| SCu, at r.t. | 100 | 100 |
| SCu, 0° C. | 100 | 100 |

At r.t: prepared at room temperature
At 0° C.: prepared at 0° C.

Example 27 Comparison of the Activity with Respect to *Staphylococcus aureus* of Different Metals and Nanoparticles According to the Invention

| | MIC (Minimal Inhibitory Concentration ) in PPB | |
|---|---|---|
| Tested sample | MRSA (Meticillin Resistant Staphylococcus Aureus) | MSSA (Meticillin Sensible Staphylococcus Aureus) |
| A | $7.81 \times 10^{-4}$ | $7.81 \times 10^{-4}$ |
| B | 0.05 | 0.05 |
| C | $1.95 \times 10^{-4}$ | $4.88 \times 10^{-5}$ |
| D | 0.05 | 0.05 |
| E | no inhibition | no inhibition |
| F | $9.71 \times 10^{-5}$ | $4.88 \times 10^{-5}$ |
| G | $9.71 \times 10^{-5}$ | $4.88 \times 10^{-5}$ |
| H | $3.9 \times 10^{-4}$ | $4.88 \times 10^{-5}$ |

A: Ag 0.2 g/L
B: Ag 0.2 g/L PEG dithiol pH = 7
C: $Ag_2S$/Ag 0.2 g/L/CTAB
D: S 0.2 g/L in presence of PEG-60 (S/PEG)
E: S 0.2 g/L (S 0.2 g/L/PEG-dithiol)
F: Cu 0.2 g/L/CTAB 20% glycerol pH = 7
G: Cu 0.2 g/L/CTAB pH = 7
H: Au 0.2 g/L/CTAB 0.2 g/L

The invention claimed is:

1. Method of treatment of bacterial, or of fungal diseases, comprising administrating a transition metal in insoluble form to a patient in need thereof,
    wherein the transition metal in insoluble form is in the form of a transition metal with oxidation state 0 or in the form of a sulfide or a transition metal oxide,
    wherein the transition metal is selected from the group consisting of copper, silver and gold,
    wherein said transition metal in insoluble form is put into aqueous solution by the formation of nanoparticles by adding surfactant, and
    wherein said transition metal is contained in a structure consisting of a core containing said transition metal, surrounded by a surfactant shell.

2. The method according to claim 1, wherein the bacterial disease is acne.

3. The method according to claim 1, wherein the surfactant is selected from an RX, X being a derived radical of a mineral or organic acid, or $NO_3^-$, $SO_4^-$, $CH_3COO^-$, or X being a halogen or other acidic radical, R being a C1-C20 alkyl trimethylammonium, or wherein said surfactant is cetyltrimethylammonium or octyltrimethylammonium, a polyethylene glycol, or polyethylene glycol-dithiol.

4. The method according to claim 1, wherein the transition metal is in a composition containing water, or a composition containing water comprising in the order of 1 to 200 mg of transition metal per liter of composition.

5. The method according to claim 1, wherein the transition metal is in a composition containing water, or a composition containing water comprising in the order of 1 to 200 mg of transition metal per liter of composition, wherein the water-containing composition is an aqueous solution.

6. The method according to claim 1, wherein the transition metal is in a composition containing water, or a composition containing water comprising in the order of 1 to 200 mg of transition metal per liter of composition, wherein the water-containing composition is an emulsion or suspension.

7. The method according to claim 1, wherein the transition metal is in a composition containing water, or a composition containing water comprising in the order of 1 to 200 mg of transition metal per liter of composition, wherein the water-containing composition is an oil-in-water or water-in-oil emulsion.

8. The method according to claim 1, wherein the transition metal is in a composition containing water, or a composition containing water comprising in the order of 1 to 200 mg of transition metal per liter of composition, wherein the water-containing composition is an oil-in-water or water-in-oil emulsion, said transition metal being copper, silver or gold in the form of nanoparticles.

9. A composition containing a transition metal in insoluble form,
wherein the transition metal in insoluble form is in the form of a transition metal with oxidation state 0 or in the form of a sulfide or a transition metal oxide,
wherein the transition metal is selected from the group consisting of copper, silver and gold,
wherein said transition metal in insoluble form is put into aqueous solution by the formation of nanoparticles by adding surfactant, and
wherein said transition metal is contained in a structure consisting of a core containing said transition metal, surrounded by a surfactant shell.

10. The composition according to claim 9, wherein the surfactant is selected from an RX, X being a derived radical of a mineral or organic acid, or $NO_3^-$, $SO_4^-$, $CH_3COO^-$, or X being a halogen or other acidic radical, R being a C1-C20 alkyl trimethylammonium, or wherein said surfactant is cetyltrimethylammonium or octyltrimethylammonium, a polyethylene glycol, or polyethylene glycol-dithiol.

11. The composition according to claim 9, said composition being
a pharmaceutical composition or a veterinary composition, said pharmaceutical composition or veterinary composition optionally comprising as excipients at least one vegetable oil, or argan oil, grape seed, avocado, hemp or apricot kernels, or a cosmetic composition.

12. The composition according to claim 9, said composition being a pharmaceutical composition or a veterinary composition, wherein said transition metal is at a dose of 1 mg to 1 g of transition metal per liter of composition, or said composition being a cosmetic composition comprising in the order of 1 to 200 mg of transition metal per liter of composition.

13. The composition according to claim 9, said composition being a pharmaceutical composition or a veterinary composition, the form of administration of which is topical.

14. Method of cosmetic treatments comprising administrating a transition metal in insoluble form to a person in need thereof,
wherein the transition metal in insoluble form is in the form of a transition metal with oxidation state 0 or in the form of a sulfide or a transition metal oxide,
wherein the transition metal is selected from the group consisting of copper, silver and gold,
wherein said transition metal in insoluble form is put into aqueous solution by the formation of nanoparticles by adding surfactant, and
wherein said transition metal is contained in a structure consisting of a core containing said transition metal, surrounded by a surfactant shell.

* * * * *